US006432649B1

(12) United States Patent
Stich et al.

(10) Patent No.: US 6,432,649 B1

(45) Date of Patent: Aug. 13, 2002

(54) **METHODS FOR DETECTING *EHRLICHIA CANIS* AND *EHRLICHIA CHAFFEENSIS* IN VERTEBRATE AND INVERTEBRATE HOSTS**

(75) Inventors: Roger William Stich, Columbus; Yasuko Rikihisa, Worthington, both of OH (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 09/648,520

(22) Filed: Aug. 25, 2000

(51) Int. Cl.$^7$ .......................... C12Q 1/68; C07H 21/04

(52) U.S. Cl. ..................... 435/6; 536/24.32; 536/24.33

(58) Field of Search .......................... 435/6; 536/24.32, 536/24.33

(56) References Cited

FOREIGN PATENT DOCUMENTS

| | | | |
|---|---|---|---|
| WO | WO9913720 | * | 3/1999 |
| WO | WO0032745 | * | 6/2000 |

OTHER PUBLICATIONS

McBride et al. Molecular Cloning of the Gene for a Conserved Major Immunoractive 28–Kilodalton Protein of *Ehrlichia canis*: a Potential Serodiagnostic Antigen Clinical and Diagnostic Laboratory Immunology May 1999 p. 392–399.*

Ohashi et al. Cloning and Characterization of Muligenes Encoding the Immunodominant 30–Kilodalton Major Outer Membrane Proteins of *Ehrlichia canis* and Application of the Recombinant Protein for Serodiagnosis Journal of Clinical Microbiology Sep. 1998 p. 26.*

"Detection of *Ehrlichia canis* in *Rhipicephalus sanguineus* with a p30–based PCR Assay" by Grover, et al. Seventy–ninth Conference of Research Workers in Animal Diseases, Chicago, Illinois, Nov. 7–9, 1999.

"A Polymerase Chain Reaction Assay for *Ehlrichia Canis*" by Stich, et al., 3$^{rd}$ Annual Conference, Tick an Tick–Borne Pathogens: Into the 21$^{st}$ Centure, High Tatra Mountains, Slovakla, Aug. 30—Sep. 3, 1999.

* cited by examiner

*Primary Examiner*—Remy Yucel

*Assistant Examiner*—Konstantina Katcheves

(74) *Attorney, Agent, or Firm*—Calfee, Halter & Griswold LLP

(57) ABSTRACT

Tools and methods for detecting the presence of *E. canis* and *E. chaffeensis* in a sample obtained from an animal are provided. The methods employ a polymerase chain reaction and primer sets that are based on the p30 gene of *E. canis* and the p28 gene of *E. chaffeensis.* The present invention also relates to the p30 and the p28 primer sets. Each p30 primer set comprises a first primer and the second primer, both of which are from 15 to 35 nucleotides in length. The first p30 primer comprises a sequence which is complementary to a consecutive sequence, within the following sequence: CCA AGTGTCTCAC ATTTTGGTAG CTTCTCAGCT AAAGAAGAAA GCAAATCAAC TGTTGGAGTTTTTGGATTAA AACATGATTG GGATGGAAGT CCAATACTTA AGAATAAACA CGCTGACTTTACTGTTCCAA AC. SEQ ID NO.1. The second p30 primer comprises a sequence which is complementary to the inverse complement of a consecutive sequence contained within the following sequence: GTTACT CAATGGGTGG CCCAAGAATA GAATTCGAAA TATCTTATGA AGCATTCGAC GTAAAAAGTC CTAATATCAA TTATCAAAAT GACGCGCACA GGTACTGCGC TCTATCTCAT CACACATCGG CAGCCAT, SEQ ID NO.2. The first p28 comprises a sequence which is complementary to a consecutive sequenc, within the following sequence : A GTTTTCATAA CAAGTGCATT GATATCACTA ATATCTTCTC TACCTGGAGT ATCATTTTCC GACCCAACAG GTAGTGGTAT TAACGG, SEQ ID NO. 3. The second p28 primer comprises a sequence which is complementary to the inverse complement of a consecutive sequence within one of the following two sequences: CAT TTCTAGGTTT TGCAGGAGCT ATTGGCTACT CAATGGATGG TCCAAGAATA GAGCTTGAAG TATCTTATGA, SEQ ID NO. 4, or C AAGGAAAGTT AGGTTTAAGC TACTCTATAA GCCCAGA, SEQ ID NO. 5.

10 Claims, 11 Drawing Sheets

FIG. 1A

LOCUS AF082744 1607 bp DNA BCT 20-OCT-1998

ORIGIN

```
   1 attttattta ttaccaatct tatataatat attaaatttc tcttacaaaa atctctaatg
  61 ttttatacct aatatatata ttctggcttg tatctacttt gcacttccac tattgttaat
 121 ttattttcac tattttaggt gtaatatgaa ttgcaaaaaa attcttataa caactgcatt
 181 aatatcatta atgtactcta ttccaagcat atctttttct gatactatac aagatggtaa
 241 catgggtggt aacttctata ttagtggaaa gtatgtacca agtgtctcac attttggtag
 301 cttctcagct aaagaagaaa gcaaatcaac tgttggagtt tttggattaa aacatgattg
 361 ggatggaagt ccaatactta agaataaaca cgctgacttt actgttccaa actattcgtt
 421 cagatacgag aacaatccat ttctagggtt tgcaggagct atcggttact caatgggtgg
 481 cccaagaata gaattcgaaa tatcttatga agcattcgac gtaaaaagtc ctaatatcaa
 541 ttatcaaaat gacgcgcaca ggtactgcgc tctatctcat cacacatcgg cagccatgga
 601 agctgataaa tttgtcttct taaaaaacga agggttaatt gacatatcac ttgcaataaa
 661 tgcatgttat gatataataa atgacaaagt acctgtttct ccttatatat gcgcaggtat
 721 tggtactgat ttgatttcta tgtttgaagc tacaagtcct aaaatttcct accaaggaaa
 781 actgggcatt agttactcta ttaatccgga aacctctgtt ttcatcggtg ggcatttcca
 841 caggatcata ggtaatgagt ttagagatat tcctgcaata gtacctagta actcaactac
 901 aataagtgga ccacaatttg caacagtaac actaaatgtg tgtcactttg gtttagaact
 961 tggaggaaga tttaacttct aattttattg ttgccacata ttaaaaatga tctaaacttg
1021 tttttawtat tgctacatac aaaaaaagaa aaatagtggc aaaagaatgt agcaataaga
1081 gggggggggg ggaccaaatt tatcttctat gcttcccaag ttttttcycg ctatttatga
1141 cttaaacaac agaaggtaat atcctcacgg aaaacttatc ttcaaatatt ttatttatta
1201 ccaatcttat ataatatatt aaatttctct tacaaaaatc actagtattt tataccaaaa
1261 tatatattct gacttgcttt tcttctgcac ttctactatt tttaatttat ttgtcactat
1321 taggttataa taawatgaat tgcmaaagat ttttcatagc aagtgcattg atatcactaa
1381 tgtctttctt acctagcgta tctttttctg aatcaataca tgaagataat ataaatggta
```

FIG. 1B 1441 acttttacat tagtgcaaag tatatgccaa gtgcctcaca ctttggcgta ttttcagtta 1501 aagaagagaa aaacacaaca actggagttt tcggattaaa acaagattgg gacggagcaa 1561 cactaaagga tgcaagcwgc agccacacaw tagacccaag tacaatg

FIG. 2

Consensus sequence for Ehrlichia chaffeensis p28 ORF from Sapulpa, Jacksonville and Arkansas isolates
chaf28kcon.seq Length: 849 July 14, 1999 11:21 Type: N Check: 1874

```
  1 ATGAATTACA AAAAAGTTTT CATAACAAGT GCATTGATAT CAYTAATATC
 51 TTCTCTACCT GGAGTATCAT TTTCYGACCC ARCAGGTAGT GGTATTAACG
101 GYAATTTCTA YATCAGTGGA AAATAYATGC CAAGYGCTTC GCATTTTGGR
151 GTRTTYTCTG CTAAGGAAGA AAGAARTACA ACAGYTGGAG TRTTTGGAYT
201 GAAGCAARAT TGGGAYGGMA GYGCAATAYC YMACWCYHMY MSWRAHRMTV
251 YATTYACTGT YTCAAAYTAY TCRTTTAAAT ATGAAAAYAA YCCRTTTYTA
301 GGWTTTGCAG GAGCTATTGG YTACTCAATG GATGGYCCAA GAATAGAGCT
351 TGAAGTATCT TATGARACAT TYGATGTWAA AAATCAAGGT AACARYTAYA
401 AGAAYGAAGC DCATAGRTAY TGTGCTYTAT CYCRTMASRS YWCARBARCA
451 RRCATGWSKA GTGCARRTRA TAMWTTTGTY TTTCTAAAAA ATGAAGGRYT
501 ACTTGACRTA TCRTTYATGC TGAACGCATG CTATGAYGTA RTARGYGAAG
551 GMATACCTTT TTCTCCTTAY ATATGYGYAG GTATYGGKAC TGATTTAGTA
601 TCCATGTTTG AAGYTACAAA YCCTAAAATT TCTTACCAAG GAAAGTTAGG
651 TTTAAGCTAC TCTATAAGCC CAGAARCTTC TGTSTTTRTY GGYGGRCAYT
701 TYCATAAGGT RATRGGRAAC GAATTYAGAG ATATTCCTRC TRTAATACCT
751 AVTGGATCAA SWCTTGCAGG AAMAGGRAAY YACCCTGCAA TAGTAAYACT
801 RGAYGTATGC CACTTTGGWA TAGARCTTGG AGGAAGRTTT GCTTTCTAA
```

Fig. 4

```
Amplicon         ~~~~~~~~~~~~~~~~~~~~~~~~~AAACTATTCGTTCAGATACGAGAACAATCCATTTCTAGGGTTTGC
E. canis (Jake)  ATAAACACGCTGACTTTACTGTTCCAAACTATTCGTTCAGATACGAGAACAATCCATTTCTAGGGTTTGC
ECA30-583A       ~~~~~~~~~~~~~~~~~~~~~~~~~~~~~~~~~~~~~~~~~~~~~~~~~~~~~~~~~~~~~~~~~~~~~~
ECA30-384S       ATAAACACGCTGACTTTACTGTTCC~~~~~~~~~~~~~~~~~~~~~~~~~~~~~~~~~~~~~~~~~~~~~

Amplicon         AGGAGCTATCGGTTACTCAATGGGTGGCCCAAGAATAGAATTCGAAATATCTTATGAAGCATTCGACGTA
E. canis (Jake)  AGGAGCTATCGGTTACTCAATGGGTGGCCCAAGAATAGAATTCGAAATATCTTATGAAGCATTCGACGTA
ECA30-583A       ~~~~~~~~~~~~~~~~~~~~~~~~~~~~~~~~~~~~~~~~~~~~~~~~~~~~~~~~~~~~~~~~~~~~~~
ECA30-384S       ~~~~~~~~~~~~~~~~~~~~~~~~~~~~~~~~~~~~~~~~~~~~~~~~~~~~~~~~~~~~~~~~~~~~~~

Amplicon         AAAAGTCCTAATATCAATTATCAAAATGACGCGCACAGGTACTGCGCTCTATCTCATCAC~~~~~~~~~~
E. canis (Jake)  AAAAGTCCTAATATCAATTATCAAAATGACGCGCACAGGTACTGCGCTCTATCTCATCACACATCGGCAG
ECA30-583A       ~~~~~~~~~~~~~~~~~~~~~~~~~~~~~~~~~~~~~GGTACTGCGCTCTATCTCATCAC~~~~~~~~~~
ECA30-384S       ~~~~~~~~~~~~~~~~~~~~~~~~~~~~~~~~~~~~~~~~~~~~~~~~~~~~~~~~~~~~~~~~~~~~~~
```

METHODS FOR DETECTING *EHRLICHIA CANIS* AND *EHRLICHIA CHAFFEENSIS* IN VERTEBRATE AND INVERTEBRATE HOSTS

BACKGROUND OF THE INVENTION

The Ehrlichiae are obligate intracellular bacteria found in circulating leukocytes of infected animals. *Ehrlichia canis* (*E. canis*) infects monocytes and causes ehrlichiosis in animals belonging to the family Canidae. *E. canis* is transmitted by the brown dog tick, *Rhipicephalus sanguineus.*

Canine monocytic ehrlichiosis (CME) consists of an acute and a chronic phase. The acute phase is characterized by fever, serous nasal and ocular discharges, anorexia, depression, and loss of weight. The chronic phase is characterized by severe pancytopenia, epistaxis, hematuria, blood in feces in addition to more severe clinical signs of the acute disease. If treated early during the course of the disease, dogs respond well to doxycycline. However, chronically infected dogs do not respond well to the antibiotic. Therefore, early diagnosis is very important for treating canine ehrlichiosis.

Human monocytic ehrlichiosis (HME) is a tick-borne, emerging infectious disease that is caused by the rickettsial pathogen, *Ehrlichia chaffeensis* (*E. chaffeensis*). The course of HME begins with an asymptomatic pre-patent period, followed by an acute phase where the vertebrate host suffers pyrexia, anorexia, weight loss, cytopenia and even death. Non-human hosts that survive the acute phase typically undergo partial recovery and suffer mild chronic infections, during which they could be persistent carriers that are capable of infecting tick vectors. Both dogs and white tailed deer are susceptible to infection with *E. chaffeensis,* and both of these hosts are suspected reservoirs of this pathogen. *E. chaffeensis* appears to be transmitted by *Amblyomma. americanum,* and appears to be endemic to the southern U.S. where this tick is indigenous. Symptoms of human monocytic ehrlichiosis (HME) are similar to those of canine monocytic ehrlichiosis (CME) that is also known as tropical canine pancytopenia. (Hildebrandt, P. K., D. L. Huxsoll, et al. (1973 (1973). Pathology of canine ehrlichiosis (tropical canine pancytopenia). *Am J Vet Res* 34(10): 1309–20.; Kuehn, N. F. and S. D. Gaunt (1985). Clinical and hematologic findings in canine ehrlichiosis. *J Am Vet Med Assoc* 186(4): 355–8.; Eng, T. R., J. R. Harkess, et al. (1990). Epidemiologic, clinical, and laboratory findings of human ehrlichiosis in the United States, 1988. *Jama* 264(17): 2251–8.; McDade, J. E. (1990). Ehrlichiosis—a disease of animals and humans. *J Infect Dis* 161(4): 609–17.) The etiologic agents of CME and HME, *E. canis* and *E. chaffeensis,* respectively, have been placed in the same genogroup based on 16S rRNA sequences and antigenic cross-reactivity Anderson, B. E., J. E. Dawson, et al. (1991). *Ehrlichia chaffeensis,* a new species associated with human ehrlichiosis. *J Clin Microbiol* 29(12): 2838–42.

The primary test for diagnosing CME or HME is the indirect fluorescent antibody (IFA) test. This test uses the etiologic agents *Ehrlichia canis* or *E. chaffeensis,* respectively, to diagnose infection. The IFA test, however, has serious limitations. The IFA test is subject to false positives because the antigens are whole infected cells which comprise many nonspecific proteins that can cross-react with sera from some patients. The IFA test is also subject to false negatives because IFA antigens are unstable and may become inactivated during storage. In addition the IFA test requires a special equipment to perform the test. For example, the IFA test requires a tissue culture system for growing the bacterium that are used to prepare the antigen slides, a fluorescent microscope, and trained persons to evaluate the serum reactivity to the bacterial antigen on the slide.

Serodiagnosis is another method which has been developed to diagnose canine or human ehrlichiosis. The method involves testing the blood of the animal for antibodies immunoreactive with outer membrane proteins of these pathogens. Serodiagnosis cannot be used until the infected subject has produced such antibodies. Accordingly, serodianosis cannot be used early during the course of infection. Moreover, serodiagnosis cannot be used for detecting an ongoing infection.

Accordingly, it is desirable to have additional methods and tools which can be used for diagnosing canine and human ehrlichiosis, particularly methods and tools which can be used to detect an ongoing infection. Methods and tools which can be used to detect *E. canis* and *E. chaffeensis* in the invertebrate vectors which transmit these pathogens to their respective vertebrate hosts are also desirable.

SUMMARY OF THE INVENTION

The present invention provides tools and methods for detecting the presence of *E. canis* and *E. chaffeensis* in a sample obtained from an animal, particularly from a member of the Canidae family. The method for detecting *E. canis* comprises providing a p30 primer set comprising a first primer having a sequence which is complementary to a sequence on the *E. canis* p30 gene sense strand and a second primer which is complementary to a sequence which is complementary to a sequence on the *E. canis* p30 gene of antisense strand, amplifying DNA in the sample using a polymerase chain reaction and the p30 primer set, and determining the length or sequence of the PCR products, wherein the presence of a PCR product having a sequence or length which corresponds to the sequence or length of the region of the p30 gene which is located between the nucleotide sequences to which the first p30 primer and the second p30 primer bind is indicative of the presence of *E. canis* in the sample.

The present invention also relates to the p30 primer sets. Each p30 primer set comprises a first p30 primer and the second p30 primer, both of which are from 15 to 35 nucleotides in length. The first p30 primer, i.e., the forward primer, comprises a sequence which is complementary to a consecutive sequence, preferably of at least 14 nucleotides in length, within the following sequence: CCA AGTGTCTCAC ATTTTGGTAG CTTCTCAGCT AAAGAAGAAA GCAAATCAAC TGTTGGAGTTTTTGGATTAA AACATGATTG GGATGGAAGT CCAATACTTA AGAATAAACA CGCTGACTTTACTGTTCCAA AC. SEQ ID NO.1. The second p30 primer, i.e. the reverse primer, comprises a sequence which is complementary to the inverse complement of a consecutive sequence, preferably of at least 14 nucleotides in length, contained within the following sequence: GTTACT CAATGGGTGG CCCAAGAATA GAATTCGAAA TATCTTATGA AGCATTCGAC GTAAAAAGTC CTAATATCAA TTATCAAAAT GACGCGCACA GGTACTGCGC TCTATCTCAT CACACATCGG CAGCCAT, SEQ ID NO.2. Such primers are useful for detecting the presence of *E. canis* in members of the Canidae family. Such primers are also useful for detecting the presence of *E.canis* DNA in samples obtained from ticks or other invertebrate carriers which feed on the vertebrate hosts.

The method for detecting *E. chaffeensis* comprises providing a p28 primer set comprising a first primer comprising a sequence which is complementary to a sequence on the *E. chaffeensis* p28 gene sense strand and a second primer which is complementary to a sequence on the *E. chaffeensis* p28 gene antisense strand, amplifying DNA in the sample using a polymerase chain reaction and the p28 primer set, and determining the length or sequence of the PCR products, wherein the presence of a PCR product having a sequence or length which corresponds to the sequence or length of that portion of the p28 gene which is located between the sequence to which the first p28 primer and second p28 primer bind is indicative of the presence of *E. chaffeensis* DNA in the sample.

The present invention also relates to the primers in the p28 primer set. The first p28 and second p28 primers are from 15 to 35 nucleotides in length. The first p28 primer, i.e. the forward primer, comprises a sequence which is substantially identical to the complement of a consecutive sequence, preferably of at least 14 nucleotides in length, within the following sequence :A GTTTTCATAA CAAGTGCATT GATATCACTA ATATCTTCTC TACCTGGAGT ATCATTTTCC GACCCAACAG GTAGTGGTAT TAACGG, SEQ ID NO.3.

The second primer, i.e. the reverse primer, comprises a sequence which is complementary to the inverse complement of a consecutive sequence, preferably of at least 14 nucleotides in length, within one of the following two sequences: CAT TTCTAGGTTT TGCAGGAGCT ATTGGCTACT CAATGGATGG TCCAAGAATA GAGCTTGAAG TATCTTATGA, SEQ ID NO.4, or C AAGGAAAGTT AGGTTTAAGC TACTCTATAA GCCCAGA, SEQ ID NO.5. Such primers are useful for detecting the presence of *E. chaffeensis* in samples obtained from vertebrate animals such as humans or dogs, or from the invertebrate vectors which transmit this pathogen from one vertebrate animal to another.

BRIEF DESCRIPTION OF THE FIGURES

FIG. 1 shows the nucleotide sequence of the p30 gene (SEQ ID NO. 47) of the Jake strain of *E. canis*. (Genbank Accession No. AF082744.)

FIG. 2 is a consensus open reading frame (ORF) sequence for the *E. chaffeensis* p28 gene (SEQ ID NO. 48). The consensus sequence was derived from the p28 genes of the Sapulpa, Jacksonville and Arkansas isolates.

FIG. 4. Confirmation of the *E. canis* nested target amplicon sequence. Multiple sequence alignment of the amplicon (nucleotides 409–583 of SEQ ID NO. 47) derived from nested p30-based PCR of DNA from *E. canis* (Ebony isolate), the *E. canis* p30 target DNA sequence (Jake Isolate; nucleotides 384–593 of SEQ ID NO. 47) and primer set 1 (ECA30-384S, SEQ ID NO. 6 and ECA30-583A, reverse complement of SEQ ID NO. 7). The DNA sequence for ECA30-583A is the reverse complement of that oligonucleotide. The sequences were aligned and compared with the Pileup (GCG, version 10) and Boxshade programs. White letters surrounded by a black box represent bases that are identical in each sequence of the alignment.

echF58–79, nucleotides 58–79 of SEQ ID NO. 48; echF59–79, nucleotides 59–79 of SEQ ID NO. 48; echF59–79, nucleotides 59–79 of SEQ ID NO. 48; echF59–80, nucleotides 59–80 of SEQ ID NO. 48; echF60–80 of SEQ ID NO. 48; echF61–82, nucleotides 61–82 of SEQ ID NO. 48; echF67–85, nucleotides 67–85 of SEQ ID NO. 48; echF78–99, nucleotides 78–99 of SEQ ID NO. 48; *E. canis,* nucleotides 202–249 of SEQ ID NO. 47. In (C), sequences and their SEQ ID NOs. are as follows: *E. chaffeensis* I, II, and III, reverse complement of nucleotides 291–352 of SEQ ID NO. 48; echR313–293, reverse complement of nucleotides 293–313 of SEQ ID NO. 48; ecbR314–293, reverse complement of nucleotides 293–314 of SEQ ID NO. 48; echR314–294, reverse complement of nucleotides 294–314 of SEQ ID NO. 48; echR315–294, reverse complement of nucleotides 294–315 of SEQ ID NO. 48; echR320–302, reverse complement of nucleotides 302–320 of SEQ ID NO. 48; ecbR321–302, reverse complement of nucleotides 302–321 of SEQ ID NO. 48; echR322–302, reverse complement of nucleotides 302–322 of SEQ ID NO. 48; echR339–319, reverse complement of nucleotides 319–339 of SEQ ID NO. 48; echR341–320, reverse complement of nucleotides 320–341 of SEQ ID NO. 48; echR352–331, reverse complement of nucleotides 331–352 of SEQ ID NO. 48; *E. canis,* reverse complement of nucleotides 436–497 of SEQ ID NO. 47.

Figure 10:
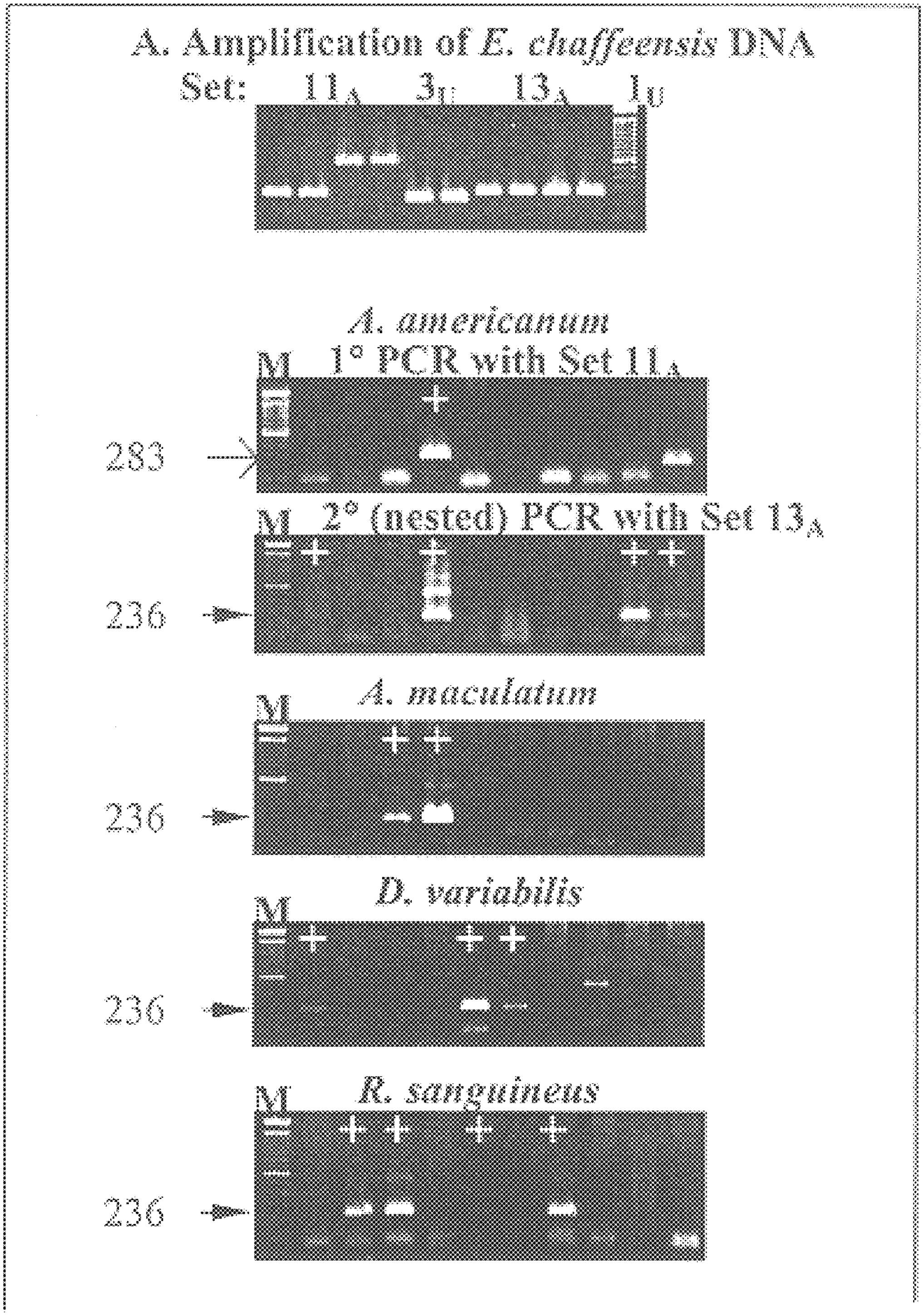

FIG. 10. shows: Detection of *E. chaffeensis* (Arkansas isolate) with the p28-based PCR assay. Panel A demonstrates amplicons from duplicate non-optimized PCR in the presence of 50 ng of DNA from *E. chaffeensis*-infected DH82 cells and various primer sets that are specific to the Arkansas isolate ($11_A$, $13_A$ and $15_A$) or universal to all three p28 clusters ($3_U$ and $1_U$), which are described in Table X. Panel B consists of male ticks of four species known to parasitize dogs that were intrastadially exposed to *E. chaffeensis* by allowing them to feed on on a rickettsemic dog followed by holding for 10 days in a humidity chamber. Both 1° and 2° optimized PCR assays are shown for *A. americanum.* PCR-positive ticks are indicated by a white "+" at the top of each lane. Note that *E. chaffeensis* infection was detected in 20–40% of each tick species tested. A 100 bp ladder served as the molecular size standard (M).

DETAILED DESCRIPTION OF THE INVENTION

In one aspect,the present invention provides methods and tools for detecting the presence of *Ehrlichia canis* in samples obtained from a vertebrate or invertebrate animal. The method comprises amplifying the DNA contained within the sample using a primer set comprising primers which comprise sequences that are complementary to select regions of the p30 gene of *E. canis* and a polymerase chain reaction (PCR) to provide a pool of PCR products, and then assaying the pool for the presence or absence of a PCR product whose length or sequence indicates that PCR product corresponds to the region of the p30 gene that is flanked by the nucleotide sequences which are complementary to the first and second members of the p30 primer set. The tools are the members of the p30 primer sets. The *E. canis* p 30 gene belongs to the omp-1 multiple gene family and has the sequence which is set forth in Genbank as Accession No. AF082744.1 (Jake isolate), Accession No. AF082750.1 (Florida isolate), Accession No. AF082749.1 (Fuzzy isolate), Accession No. AF082748.1m (DJ isolate), Accession No. AF082747.1 (Arkansas isolate), Accession No. AF082746.1 (Oklahoma isolate) and Accession No. AF082745.1 (Louisiana isolate of *E. canis.*) The *E. canis* p30 gene encodes the immunodominants ehrlichial outer membrane protein P30.

In another aspect, the present invention provides methods and tools for detecting the presence of *Ehrlichia chaffeensis* in samples obtained from vertebrate or invertebrate animals. The method comprises amplifying the DNA contained within the sample using a p28 primer set whose members comprise a sequence which is complementary to select regions of the p28 gene of *E. chaffeensis* and a polymerase chain reaction (PCR) to provide a pool of PCR products, and then assaying the pool for the presence of a PCR product whose length or sequence indicates that PCR product corresponds to the region of the p28 gene that comprises and is flanked by the nucleotide sequences to which the members of the p28 primer set bind. The tools are the members of the p28 primer sets. The *E. chaffeensis* p28 gene belongs to the omp-1 multiple gene family and has the sequence which is set forth in Genbank as (Accession No. AF077735.1 (St. Vincent isolate), Accession No. AF077734.1 (Sapulpa isolate), Accession No. AF077733.1 (Jax isolate), Accession No. AF077732.1 (91HE17 isolate) and Accession No. AF068234 (Arkansas isolate). The *E. chaffeensis* p28 gene encodes the immunodominants ehrlichial outer membrane protein P28.

Primer

The primers in the p30 primer set are based upon select sequences in the p30 gene of *E. canis.* The p30 gene encodes the major outer membrane protein of *E. canis.* The sequences of the first and second primers in the p30 primer set are distinct from sequences found in the closely related p28 gene in *E. chaffeensis.* The first primer in the p30 primer set is an oligonucleotide of from 15 to 35 nucleotides in length, preferably from 18 to 30 nucleotides in length. The second p30 primer in the *E. canis* primer set is an oligonucleotide of from 15 to 35 nucleotides, preferably from 18 to 30 nucleotides in length. The first p30 primer, i.e., the forward primer, comprises a sequence which is substantially identical to the complement of consecutive sequence located between nucleotides 278 and 412 of the sense strand of the open reading frame sequence of the p30 gene of *E. canis.* The sequence of the sense strand in this region is as follows: CCA AGTGTCTCAC ATTTTGGTAG CTTCTCAGCT AAAGAAGAAA GCAAATCAAC TGTTGGAGTT TTTGGATTAA AACATGATTG GGATGGAAGT CCAATACTTA AGAATAAACA CGCTGACTTT ACTGT-TCCAA AC. SEQ ID NO.1 As used herein the term "substantially identical" means that the sequence is at least 90% identical, preferably at least 95% identical, more preferably 100% identical to a particular reference sequence, e.g., to the complement of a consecutive sequence contained within SEQ ID NO. 1. The second p30 primer, i.e., the reverse primer, comprises a sequence which is substantially identical to and the inverse of a consecutive sequence located between nucleotides 465 through 597 of the sense strand of the p30 gene of *E. canis.* The sequence of the second p30 primer is substantially identical to the complement of the inverse complement of a consecutive sequence contained within the following sequence: GTTACT CAATGGGTGG CCCAAGAATA GAATTCGAAA TATCTTATGA AGCAT-TCGAC GTAAAAAGTC CTAATATCAA TTATCAAAAT GACGCGCACA GGTACTGCGC TCTATCTCAT CACA-CATCGG CAGCCAT, SEQ ID NO.2.

In specific embodiments, the first and second primers in the p30 primer set comprise the sequences shown in Table 1 below. The first and second primers may also comprise sequences which are shorter by one or two oligonucleotides than the sequences shown in Table 1 below. The first and second primers of the *E. canis* primer set may also comprise a sequence which is longer than the sequences shown in Table 1 below. Such sequences have one or two additional nucleotides attached to the 5' end of the above-listed sequences. The additional nucleotides are selected from the group consisting of adenylic acid, guanylic acid, and combinations thereof The sequence of the thirteen *E. canis* p30 primer sets shown in Table 1 below are based upon a comparison of the open-reading frame sequences of the seven *E. canis* and five *E. chaffeensis* isolates. It is expected that such primer sets will specifically amplify the target sequence of multiple *E. canis* isolates, but not the *E. chaffeensis* isolates. It is expected that the primers shown in Table 1 below are both species-universal and species-specific for *E. canis.* In accordance with the present invention, it has been determined that amplification of DNA isolated from *E. chaffeensis, E. muris,* and the HGE agent with these primer sets failed to produce a PCR product that is diagnostic of *E. canis.*

TABLE 1

Oligonucleotide sequences of *E. canis* p30 primer sets.

| Set | Forward | Reverse |
|---|---|---|
| 1 | ECA30-384S (SEQ ID NO.6) (ATAAACACGCTGACTTTACTGTTCC) | ECA30-583A (SEQ ID NO.7) (GTGATGAGATAGAGCGCAGTACC) |
| 2 | ECA30-387S (SEQ ID NO.8) (AACACGCTGACTTTACTGTTCC) | ECA30-597A (SEQ ID NO.9) (ATGGCTGCCGATGTGTGATG) |
| 3 | ECA30-390S (SEQ ID NO.10) (ACGCTGACTTTACTGTTCCAAAC) | ECA30-597A (SEQ ID NO.9) (ATGGCTGCCGATGTGTGATG) |
| 4 | ECA30-351S (SEQ ID NO.11) (AACATGATTGGGATGGAAGTC) | ECA30-591A (SEQ ID NO.12) (GCCGATGTGTGATGAGATAG) |
| 5 | ECA30-350S (SEQ ID NO.13) (AAACATGATTGGGATGGAAGTC) | ECA30-591bA (SEQ ID NO.14) (GCCGATGTGTGATGAGATAGAG) |
| 6 | ECA30-356S (SEQ ID NO.15) (GATTGGGATGGAAGTCCAATAC) | ECA30-591A (SEQ ID NO.12) |
| 7 | ECA30-356S (SEQ ID NO.15) | ECA30-591bA (SEQ ID NO.14) |
| 8 | ECA30-388S (SEQ ID NO.16) (ACACGCTGACTTTACTGTTCCAAAC) | ECA30-597bA (SEQ ID NO.17) (ATGGCTGCCGATGTGTGATGAG) |
| 9 | ECA30-282S (SEQ ID NO.18) (GTGTCTCACATTTTGGTAGCTTCTC) | ECA30-486A (SEQ ID NO.19) (CTTGGGCCACCCATTGAGTAAC) |
| 10 | ECA30-356S (SEQ ID NO.15) (CGATGTGTGATGAGATAGAGC) | ECA30-589A (SEQ ID NO.20) |
| 11 | ECA30-355S (SEQ ID NO.21) (TGATTGGGATGGAAGTCCAATAC) | ECA30-589bA (SEQ ID NO.22) (CGATGTGTGATGAGATAGAGCG) |
| 12 | ECA30-353S (SEQ ID NO.23) (CATGATTGGGATGGAAGTCCAATAC) | ECA30-597A (SEQ ID NO.9) (ATGGCTGCCGATGTGTGATG) |
| 13 | ECA30-278S (SEQ ID NO.24) (CCAAGTGTCTCACATTTTGGTAGC) | ECA30-484A (SEQ ID NO.25) (TGGGCCACCCATTGAGTAAC) |

The predicted annealing scores and specificity values, as compared to the p28 of *E. chaffeensis,* of these primer sets are shown in Table 2 below.

TABLE 2

Ranks of *E. canis* p30 primer sets with predicted annealing and specificity values.

| Primer | Identity Scores to *E. chaffeensis*[a] | | | | | | | Total | |
|---|---|---|---|---|---|---|---|---|---|
| | Cluster I | | Cluster II | | Cluster III | | | Annealing | |
| Set | Forward | Reverse | Forward | Reverse | Forward | Reverse | Mean[b] | Score[c] | Rank[d] |
| 1 | 0.64 | 0.74 | 0.48 | 0.87 | 0.56 | 0.78 | 0.68 | 52 | 2 |
| 2 | 0.59 | 0.45 | 0.55 | 0.65 | 0.55 | 0.60 | 0.56 | 57 | 1 |
| 3 | 0.74 | 0.45 | 0.61 | 0.65 | 0.70 | 0.60 | 0.62 | 58 | 3 |
| 4 | 0.81 | 0.55 | 0.86 | 0.75 | 0.71 | 0.70 | 0.73 | 63 | 5 |
| 5 | 0.82 | 0.55 | 0.82 | 0.77 | 0.73 | 0.73 | 0.74 | 64 | 6 |
| 6 | 0.91 | 0.55 | 0.86 | 0.75 | 0.77 | 0.70 | 0.76 | 64 | 7 |
| 7 | 0.91 | 0.55 | 0.86 | 0.77 | 0.77 | 0.73 | 0.76 | 65 | 9 |

TABLE 2-continued

Ranks of *E. canis* p30 primer sets with predicted annealing and specificity values.

| Primer Set | Identity Scores to *E. chaffeensis*[a] Cluster I Forward | Cluster I Reverse | Cluster II Forward | Cluster II Reverse | Cluster III Forward | Cluster III Reverse | Mean[b] | Total Annealing Score[c] | Rank[d] |
|---|---|---|---|---|---|---|---|---|---|
| 8 | 0.68 | 0.45 | 0.60 | 0.68 | 0.68 | 0.64 | 0.62 | 66 | 4 |
| 9 | 0.64 | 0.86 | 0.64 | 0.95 | 0.72 | 0.91 | 0.79 | 67 | 12 |
| 10 | 0.91 | 0.62 | 0.86 | 0.81 | 0.77 | 0.71 | 0.78 | 67 | 10 |
| 11 | 0.87 | 0.64 | 0.83 | 0.82 | 0.74 | 0.73 | 0.77 | 68 | 11 |
| 12 | 0.88 | 0.45 | 0.84 | 0.65 | 0.80 | 0.70 | 0.72 | 68 | 8 |
| 13 | 0.67 | 0.85 | 0.67 | 0.95 | 0.71 | 0.90 | 0.79 | 68 | 13 |

[a]Identity Score = No. oligonucleotide bases identical to aligned template ÷ total No. oligonucleotide bases.
[b]Mean identity score for both primers of each set to all three *E. chaffeensis* clusters.
[c]Determined by GCG (version 10) Prime program. Sum of annealing scores for primer secondary structure, non-specific primer binding to the template sequence and self-complementarity of individual primers and complementarity between primer pairs; the lowest scores indicate the primer sets with least complementarity to sequences other than the target binding site.
[d]Rank determined by product of annealing score and mean identity score; lower values have higher rank.

The primers in the *E. chaffeensis* p28 primer set are based upon select sequences in the p28 gene of *E. chaffeensis.* The p28 gene encodes a major outer membrane protein of *E. chaffeensis.* The sequences of the first and second primers in the p28 primer set are distinct from sequences found in the closely related p30 gene in *E. canis.* The first primer in the p28 primer set is an oligonucleotide of from 15 to 35 nucleotides in length., preferably from 18 to 30 nucleotides in length. The second primer in the *E. chaffeensis* p 28 primer set is an oligonucleotide of from 15 to 35 nucleotides, preferably from 18 to 30 nucleotides in length. The first p28 primer, i.e., the forward primer, comprises a sequence which is substantially identical to the complement of consecutive sequence located between nucleotides 15 and 101 of the sense strand of the open reading frame sequence of the p28 gene of *E. chaffeensis.* The sequence of the sense strand in this region is as follows: A GTTTTCATAA CAAGTGCATT GATATCACTA ATATCTTCTC TACCTGGAGT ATCATTTTCC GACCCAACAG GTAGTGGTAT TAACGG, SEQ ID NO. 3.

The second p28 primer, i.e., the reverse primer, comprises a sequence which is substantially identical to and the inverse of a consecutive sequence located between nucleotides 341 through 365 or nucleotides 641 through 674 of the sense strand of the p28 gene of *E. chaffeensis.* The sequence of the second p28 primer is substantially identical to the complement of the inverse complement of a consecutive sequence contained within one of the following two sequences: CAT TTCTAGGTTT TGCAGGAGCT ATTGGCTACT CAATGGATGG TCCAAGAATA GAGCTTGAAG TATCTTATGA, SEQ ID NO. 4, or C AAGGAAAGTT AGGTTTAAGC TACTCTATAA GCCCAGA, SEQ ID NO. 5.

In specific embodiments, the first and second primers in the *E. chaffeensis* p28 primer set comprise the sequences shown in Table 3 below. The first and second primers may also comprise sequences which are shorter by one or two oligonucleotides than the sequences shown in Table 3 below. The first and second primers of the *E. chaffeensis* p28 primer set may also comprise a sequence which is longer than the sequences shown in Table 3 below. Such sequences have one or two additional nucleotides attached to the 5' end of the above-listed sequences. The additional nucleotides are selected from the group consisting of adenylic acid, guanylic acid, and combinations thereof

TABLE 3

Product: 1

[DNA] = 50.000 nM [salt] = 50.000 mM

PRIMERS

| | 5' | 3' |
|---|---|---|
| forward primer (18-mer): | 84 AGGTAGTGGTATTAACGG | 101 (SEQ ID NO. 26) |
| reverse primer (20-mer): | 360 AGATACTTCAAGCTCTATTC | 341 (SEQ ID NO. 27) |
| | forward | reverse |
| primer % GC: | 44.4 | 35.0 |
| primer Tm (degrees Celsius): | 44.4 | 43.6 |

PRODUCT

| | |
|---|---|
| product length: | 277 |
| product % GC: | 31.0 |
| product Tm: | 70.2 degrees Celsius |
| difference in primer Tm: | 0.8 degrees Celsius |
| annealing score: | 57 |
| optimal annealing temperature: | 47.3 degrees Celsius |

TABLE 3-continued

Product: 2

[DNA] = 50.000 nM [salt] = 50.000 mM

PRIMERS

| | 5' | 3' |
|---|---|---|
| forward primer (18-mer): | 84 AGGTAGTGGTATTAACGG | 101 (SEQ ID NO. 26) |
| reverse primer (20-mer): | 365 TCATAAGATACTTCAAGCTC | 346 (SEQ ID NO. 28) |
| | forward | reverse |
| primer % GC: | 44.4 | 35.0 |
| primer Tm (degrees Celsius): | 44.4 | 44.0 |

PRODUCT

| | |
|---|---|
| product length: | 282 |
| product % GC: | 30.9 |
| product Tm: | 70.2 degrees Celsius |
| difference in primer Tm: | 0.5 degrees Celsius |
| annealing score: | 57 |
| optimal annealing temperature: | 47.4 degrees Celsius |

Product: 3

[DNA] = 50.000 nM [salt] = 50.000 mM

PRIMERS

| | 5' | 3' |
|---|---|---|
| forward primer (19-mer): | 50 CTTCTCTACCTGGAGTATC | 68 (SEQ ID NO. 29) |
| reverse primer (21-mer): | 669 GCTTATAGAGTAGCTTAAACC | 649 (SEQ ID NO. 30) |
| | forward | reverse |
| primer % GC: | 47.4 | 38.1 |
| primer Tm (degrees Celsius): | 44.8 | 45.5 |

PRODUCT

| | |
|---|---|
| product length: | 620 |
| product % GC: | 30.0 |
| product Tm: | 71.1 degrees Celsius |
| difference in primer Tm: | 0.8 degrees Celsius |
| annealing score: | 61 |
| optimal annealing temperature: | 48.3 degrees Celsius |

Product: 4

[DNA] = 50.000 nM [salt] = 50.000 mM

PRIMERS

| | 5' | 3' |
|---|---|---|
| forward primer (18-mer): | 83 CAGGTAGTGGTATTAACG | 100 (SEQ ID NO. 31) |
| reverse primer (19-mer): | 364 CATAAGATACTTCAAGCTC | 346 (SEQ ID NO. 32) |
| | forward | reverse |
| primer % GC: | 44.4 | 36.8 |
| primer Tm (degrees Celsius): | 43.6 | 42.2 |

PRODUCT

| | |
|---|---|
| product length: | 282 |
| product % GC: | 31.2 |
| product Tm: | 70.3 degrees Celsius |
| difference in primer Tm: | 1.4 degrees Celsius |
| annealing score: | 63 |
| optimal annealing temperature: | 47.0 degrees Celsius |

Product: 5

[DNA] = 50.000 nM [salt] = 50.000 mM

PRIMERS

| | 5' | 3' |
|---|---|---|
| forward primer (18-mer): | 83 CAGGTAGTGGTATTAACG | 100 (SEQ ID NO. 31) |
| reverse primer (19-mer): | 359 GATACTTCAAGCTCTATTC | 341 (SEQ ID NO. 33) |
| | forward | reverse |
| primer % GC: | 44.4 | 36.8 |
| primer Tm (degrees Celsius): | 43.6 | 41.9 |

PRODUCT

| | |
|---|---|
| product length: | 277 |
| product % GC: | 31.4 |
| product Tm: | 70.3 degrees Celsius |
| difference in primer Tm: | 1.7 degrees Celsius |
| annealing score: | 63 |

TABLE 3-continued

| | | |
|---|---|---|
| optimal annealing temperature: | 46.9 degrees Celsius | |

Product: 6

[DNA] = 50.000 nM [salt] = 50.000 mM

PRIMERS

| | 5' | 3' |
|---|---|---|
| forward primer (19-mer): | 50 CTTCTCTACCTGGAGTATC | 68 (SEQ ID NO. 29) |
| reverse primer (20-mer): | 669 GCTTATAGAGTAGCTTAAAC | 650 (SEQ ID NO. 34) |
| | forward | reverse |
| primer % GC: | 47.4 | 35.0 |
| primer Tm (degrees Celsius): | 44.8 | 42.8 |

PRODUCT

| | |
|---|---|
| product length: | 620 |
| product % GC: | 30.0 |
| product Tm: | 71.1 degrees Celsius |
| difference in primer Tm: | 2.0 degrees Celsius |
| annealing score: | 63 |
| optimal annealing temperature: | 47.7 degrees Celsius |

Product: 7

[DNA] = 50.000 nM [salt] = 50.000 mM

PRIMERS

| | 5' | 3' |
|---|---|---|
| forward primer (19-mer): | 55 CTACCTGGAGTATCATTTTC | 74 (SEQ ID NO. 35) |
| reverse primer (21-mer): | 670 GGCTTATAGAGTAGCTTAAAC | 650 (SEQ ID NO. 36) |
| | forward | reverse |
| primer % GC: | 40.0 | 38.1 |
| primer Tm (degrees Celsius): | 44.7 | 45.5 |

PRODUCT

| | |
|---|---|
| product length: | 616 |
| product % GC: | 30.0 |
| product Tm: | 71.1 degrees Celsius |
| difference in primer Tm: | 0.9 degrees Celsius |
| annealing score: | 64 |
| optimal annealing temperature: | 48.3 degrees Celsius |

Product: 8

[DNA] = 50.000 nM [salt] = 50.000 mM

PRIMERS

| | 5' | 3' |
|---|---|---|
| forward primer (18-mer): | 45 AATATCTTCTCTACCTGG | 62 (SEQ ID NO. 37) |
| reverse primer (19-mer): | 359 GATACTTCAAGCTCTATTC | 341 (SEQ ID NO. 33) |
| | forward | reverse |
| primer % GC: | 38.9 | 36.8 |
| primer Tm (degrees Celsius): | 40.8 | 41.9 |

PRODUCT

| | |
|---|---|
| product length: | 315 |
| product % GC: | 32.1 |
| product Tm: | 70.9 degrees Celsius |
| difference in primer Tm: | 1.1 degrees Celsius |
| annealing score: | 65 |
| optimal annealing temperature: | 47.0 degrees Celsius |

Product: 9

[DNA] = 50.000 nM [salt] = 50.000 mM

PRIMERS

| | 5' | 3' |
|---|---|---|
| forward primer (18-mer): | 15 AGTTTTCATAACAAGTGC | 32 (SEQ ID NO. 38) |
| reverse primer (19-mer): | 364 CATAAGATACTTCAAGCTC | 346 (SEQ ID NO. 32) |
| | forward | reverse |
| primer % GC: | 33.3 | 36.8 |
| primer Tm (degrees Celsius): | 42.5 | 42.2 |

PRODUCT

| | |
|---|---|
| product length: | 350 |
| product % GC: | 31.4 |
| product Tm: | 70.9 degrees Celsius |
| difference in primer Tm: | 0.3 degrees Celsius |

TABLE 3-continued annealing score: 66
optimal annealing temperature: 47.4 degrees Celsius Product: 10

[DNA] = 50.000 nM [salt] = 50.000 mM

PRIMERS

| | 5' | 3' |
|---|---|---|
| forward primer (18-mer): | 15 AGTTTTCATAACAAGTGC | 32 (SEQ ID NO. 38) |
| reverse primer (19-mer): | 359 GATACTTCAAGCTCTATTC | 341 (SEQ ID NO. 33) |
| | forward | reverse |
| primer % GC: | 33.3 | 36.8 |
| primer Tm (degrees Celsius): | 42.5 | 41.9 |

PRODUCT product length: 345
product % GC: 31.6
product Tm: 70.9 degrees Celsius
difference in primer Tm: 0.6 degrees Celsius
annealing score: 66
optimal annealing temperature: 47.3 degrees Celsius Product: 11

[DNA] = 50.000 nM [salt] = 50.000 mM

PRIMERS

| | 5' | 3' |
|---|---|---|
| forward primer (25-mer): | 50 CTTCTCTACCTGGAGTATCATTTTC | 74 (SEQ ID NO. 39) |
| reverse primer (26-mer): | 662 GAGTAGCTTAAACCTAACTTTCCTTG | 637 (SEQ ID NO. 40) |
| | forward | reverse |
| primer % GC: | 40.0 | 38.5 |
| primer Tm (degrees Celsius): | 50.9 | 52.1 |

PRODUCT product length: 613
product % GC: 30.0
product Tm: 71.1 degrees Celsius
difference in primer Tm: 1.2 degrees Celsius
annealing score: 67
optimal annealing temperature: 50.1 degrees Celsius Product: 12

[DNA] = 50.000 nM [salt] = 50.000 mM

PRIMERS

| | 5' | 3' |
|---|---|---|
| forward primer (19-mer): | 50 CTTCTCTACCTGGAGTATC | 68 (SEQ ID NO. 29) |
| reverse primer (22-mer): | 662 GAGTAGCTTAAACCTAACTTTC | 641 (SEQ ID NO. 41) |
| | forward | reverse |
| primer % GC: | 47.4 | 36.4 |
| primer Tm (degrees Celsius): | 44.8 | 46.6 |

PRODUCT product length: 613
product % GC: 30.0
product Tm: 71.1 degrees Celsius
difference in primer Tm: 1.8 degrees Celsius
annealing score: 67
optimal annealing temperature: 48.3 degrees Celsius Product: 13

[DNA] = 50.000 nM [salt] = 50.000 mM

PRIMERS

| | 5' | 3' |
|---|---|---|
| forward primer (18-mer): | 45 AATATCTTCTCTACCTGG | 62 (SEQ ID NC. 37) |
| reverse primer (18-mer): | 365 TCATAAGATACTTCAAGC | 348 (SEQ ID NO. 42) |
| | forward | reverse |
| primer % GC: | 38.9 | 33.3 |
| primer Tm (degrees Celsius): | 40.8 | 40.2 |

PRODUCT product length: 321
product % GC: 31.8
product Tm: 70.8 degrees Celsius

TABLE 3-continued

| | | |
|---|---|---|
| difference in primer Tm: | 0.6 degrees Celsius | |
| annealing score: | 68 | |
| optimal annealing temperature: | 46.7 degrees Celsius | |

Product: 14

[DNA] = 50.000 nM [salt] = 50.000 mM

PRIMERS

| | 5' | 3' |
|---|---|---|
| forward primer (18-mer): | 45 AATATCTTCTCTACCTGG | 62 (SEQ ID NO. 37) |
| reverse primer (19-mer): | 364 CATAAGATACTTCAAGCTC | 346 (SEQ ID NO. 32) |
| | forward | reverse |
| primer % GC: | 38.9 | 36.8 |
| primer Tm (degrees Celsius): | 40.8 | 42.2 |

PRODUCT

| | |
|---|---|
| product length: | 320 |
| product % GC: | 31.9 |
| product Tm: | 70.9 degrees Celsius |
| difference in primer Tm: | 1.4 degrees Celsius |
| annealing score: | 69 |
| optimal annealing temperature: | 47.0 degrees Celsius |

Product: 15

[DNA] = 50.000 nM [salt] = 50.000 mM

PRIMERS

| | 5' | 3' |
|---|---|---|
| forward primer (24-mer): | 51 TTCTCTACCTGGAGTATCATTTTC | 74(SEQ ID NO. 50) |
| reverse primer (26-mer): | 670 GGCTTATAGAGTAGCTTAAACCTAAC | 645 (SEQ ID NO. 51) |
| | forward | reverse |
| primer % GC: | 37.5 | 38.5 |
| primer Tm (degrees Celsius): | 49.8 | 51.3 |

PRODUCT

| | |
|---|---|
| product length: | 620 |
| product % GC: | 30.0 |
| product Tm: | 71.1 degrees Celsius |
| difference in primer Tm: | 1.5 degrees Celsius |
| annealing score: | 69 |
| optimal annealing temperature: | 49.8 degrees Celsius |

Product: 16

[DNA] = 50.000 nM [salt] = 50.000 mM

PRIMERS

| | 5' | 3' |
|---|---|---|
| forward primer (22-mer): | 53 CTCTACCTGGAGTATCATTTTC | 74 (SEQ ID NO. 43) |
| reverse primer (22-mer): | 670 GGCTTATAGAGTAGCTTAAACC | 649 (SEQ ID NO. 49) |
| | forward | reverse |
| primer % GC: | 40.9 | 40.9 |
| primer Tm (degrees Celsius): | 47.7 | 48.1 |

PRODUCT

| | |
|---|---|
| product length: | 618 |
| product % GC: | 30.1 |
| product Tm: | 71.2 degrees Celsius |
| difference in primer Tm: | 0.4 degrees Celsius |
| annealing score: | 71 |
| optimal annealing temperature: | 49.2 degrees Celsius |

Product: 17

[DNA] = 50.000 nM [salt] = 50.000 mM

PRIMERS

| | 5' | 3' |
|---|---|---|
| forward primer (22-mer): | 53 CTCTACCTGGAGTATCATTTTC | 74 (SEQ ID NO. 43) |
| reverse primer (22-mer): | 662 GAGTAGCTTAAACCTAACTTTC | 641 (SEQ ID NO. 41) |
| | forward | reverse |
| primer % GC: | 40.9 | 36.4 |
| primer Tm (degrees Celsius): | 47.7 | 46.6 |

PRODUCT

| | |
|---|---|
| product length: | 610 |
| product % GC: | 30.0 |

TABLE 3-continued

| | | |
|---|---|---|
| product Tm: | 71.1 degrees Celsius | |
| difference in primer Tm: | 1.1 degrees Celsius | |
| annealing score: | 71 | |
| optimal annealing temperature: | 48.8 degrees Celsius | |

Product: 18

[DNA] = 50.000 nM [salt] = 50.000 mM

PRIMERS

| | 5' | 3' |
|---|---|---|
| forward primer (18-mer): | 57 ACCTGGAGTATCATTTTC | 74 (SEQ ID NO. 44) |
| reverse primer (18-mer): | 674 TCTGGGCTTATAGAGTAG | 657 (SEQ ID NO. 45) |
| | forward | reverse |
| primer % GC: | 38.9 | 44.4 |
| primer Tm (degrees Celsius): | 42.6 | 43.0 |

PRODUCT

| | |
|---|---|
| product length: | 618 |
| product % GC: | 30.1 |
| product Tm: | 71.2 degrees Celsius |
| difference in primer Tm: | 0.4 degrees Celsius |
| annealing score: | 73 |
| optimal annealing temperature: | 47.7 degrees Celsius |

Product: 19

[DNA] = 50.000 nM [salt] = 50.000 mM

PRIMERS

| | 5' | 3' |
|---|---|---|
| forward primer (19-mer): | 50 CTTCTCTACCTGGAGTATC | 68 (SEQ ID NO. 29) |
| reverse primer (18-mer): | 673 CTGGGCTTATAGAGTAGC | 656 (SEQ ID NO. 46) |
| | forward | reverse |
| primer % GC: | 47.4 | 50.0 |
| primer Tm (degrees Celsius): | 44.8 | 45.1 |

PRODUCT

| | |
|---|---|
| product length: | 624 |
| product % GC: | 30.3 |
| product Tm: | 71.2 degrees Celsius |
| difference in primer Tm: | 0.4 degrees Celsius |
| annealing score: | 73 |
| optimal annealing temperature: | 48.4 degrees Celsius |

Product: 20

[DNA] = 50.000 nM [salt] = 50.000 mM

PRIMERS

| | 5' | 3' |
|---|---|---|
| forward primer (18-mer): | 55 CTACCTGGAGTATCATTTTC | 74 (SEQ ID NO. 35) |
| reverse primer (19-mer): | 673 CTGGGCTTATAGAGTAGC | 656 (SEQ ID NO. 46) |
| | forward | reverse |
| primer % GC: | 40.0 | 50.0 |
| primer Tm (degrees Celsius): | 44.7 | 45.1 |

PRODUCT

| | |
|---|---|
| product length: | 619 |
| product % GC: | 30.2 |
| product Tm: | 71.2 degrees Celsius |
| difference in primer Tm: | 0.5 degrees Celsius |
| annealing score: | 75 |
| optimal annealing temperature: | 48.3 degrees Celsius |

Sample

For the vertebrate hosts the sample is a tissue sample or bodily fluid, such as for example, buffy coats and peripheral blood mononuclear cells. For the invertebrate vectors which may transmit the pathogen from one vertebrate host to another, the sample can be dissected from ticks (e.g., midgut, salivary glands and hemolymph), ticks can be cut into pieces, and ticks can be frozen and smashed in preparation for PCR assay. Further preparation of tick tissues may involve just heating the sample, digesting the samples with proteinase or isolating pure DNA from the tick tissues.

Methods

Optionally, DNA is extracted from the sample using standard methods. For example, DNA may be extracted from fluids using commercially available PCR filters such as, for example, the Isocode filters which are available from Schleicher and Schuell, New Hampshire Methods of extracting DNA from tissue samples, are also described in Maniatis, T., J. Sambrook, and E. F. Fritsch. 1989. Molecular Cloning: a Laboratory manual, 2nd ed. Cold Spring Harbor Laboratory Press, Cold Spring Harbor N.Y., which is specifically incorporated herein by reference. An optimal method for vertebrates involves collection of whole blood in the presence of an anticoagulant such as heparin, collecting the buffy coat fraction from the whole blood, removal of host hemoglobin by hypotonic lysis of erythrocytes remaining with the buffy coat followed by several washings of the buffy coat prior to preparation of the template for PCR assay. For detecting the pathogens in the invertebrate vectors, DNA is extracted from tick halves, salivary glands and midgut by digestion with proteinase K in the presence of nonionic detergents such as Tween-20 and NP-40 followed by heat inactivation of the proteinase and an optional procedure to extract proteins with phenol and chloroform followed by DNA precipitation by salt and ethanol.

The DNA is then amplified with the one of the primer sets at PCR conditions equivalent to or comparable to denaturation for 0.5 to 1.0 minute at 94° C. in a solution, followed by annealing at about 50–72° C. for 0.5 to 1.0 minutes. As recognized in the art, suitable stringency conditions can be attained by varying a number of factors such as the length and nature, i.e., DNA or RNA, of the primer; the length and nature of the target sequence; the concentration of the salts and other components of the PCR solution; the temperature and time of each step, e.g., denaturation, annealing, and elongation. All of these factors may be varied to generate conditions of stringency which are equivalent to the conditions listed above. Changes in stringency are accomplished primarily through the manipulation of annealing temperature and time.

Thereafter, the size of the PCR products is determined. Preferably the size of the PCR products is determined using gel electrophoresis and a plurality of DNA standards of varying sizes. The PCR products and DNA standards that are present on the gel are visualized using standard techniques, such as ethidium bromide staining. Optionally, the PCR products may be separated, preferably by gel electrophoresis and the sequence of the PCR products determined using standard techniques.

To further enhance the sensitivity and specificity of the method for detecting *E. canis,* a nested PCR assay which employs two different *E. canis* primer sets is used. In such assay, the sample is first amplified with a primer set comprising two external primers, i. e. ECA30-351S and ECA30-591A, ECA30-350S and ECA30-59lbA, ECA30-356S and ECA30-591A, ECA30-356S and ECA30-591Ba, ECA30-356S and ECA30-589A, ECA30-355S and ECA30-589bA, and ECA30-353S and ECA30-597A. Thereafter, the products of the first PCR are amplified with a second primer set that comprises internal primers, eg. ECA30-384S and ECA30. A highly preferred primer set for this second amplification comprises a first primer comprising the sequence 5'-ATAAACACGCTGACTTTACTGTTCC-3' (SEQ ID NO. 6) and a second primer of comprising the sequence 5'-GTGATGAGATAGAGCGCAGTACC-3' (SEQ ID NO. 7). Following the second amplification, the size or sequence of the PCR products are determined to detect a PCR product which indicates that a DNA molecule having a sequence which corresponds to the region of the p30 gene that is located between the consecutive sequences to which the internal primers bind is present in the sample.

To further enhance the sensitivity and specificity of the method for detecting *E. chaffeensis,* a nested PCR assay which employs two different *E. chaffeensis* primer sets is used. In such assay, the sample is first amplified with a primer set that comprises external primers, i.e. *E. chaffeensis* primer set 3. A highly preferred primer set for this first amplification comprises a first primer comprising the sequence CTTCTCTACCTGGAGTATC (SEQ ID NO. 29) and a second primer comprising the sequence GCTTATA-GAGTAGCTTAAACC (SEQ ID NO. 30). Thereafter, the products of the first PCR are amplified with a second primer set that comprises two internal primers, e.g. *E. chaffeensis* primer set 1. A highly preferred primer set for this second amplification comprises a first primer comprising the sequence AGGTAGTGGTATTAACGG (SEQ ID NO. 26) and a second primer which comprises the sequence AGATACTTCAAGCTCTATTC (SEQ ID NO. 27). Following the second amplification, the size or sequence of the PCR products are determined to detect a PCR product which indicates that a DNA molecule having a sequence which corresponds to 277 bp of the p28 gene is present in the sample.

EXAMPLES

The following examples are for purposes of illustration only and are not intended to limit the scope of the invention as defined in the claims which are appended hereto. The references cited in this document are specifically incorporated herein by reference.

Example 1

A. Obtaining DNA from Blood Samples of Infected Animals

Two colony-reared Beagle dogs that were seronegative for exposure to *E. canis* by IFA were inoculated with heparinized blood from a donor dog infected with *E. canis* (Ebony isolate). Heparinized blood was collected from each animal and split into 0.5 ml aliquots and subjected to the following treatments: (1) DNAzol extraction of buffy coat, (2) DNAzol-BD (Molecular Research Center) extraction of whole blood, (3) DNAzol-BD extraction of buffy coat, (4) spin-column purification of peripheral blood mononuclear cell DNA with a QIAamp Kit (Qiagen) and (5) phenol/chloroform extraction followed by ethanol precipitation of buffy coat samples. All sample preparation methods were done in duplicate and in two trials. Buffy coats were isolated from the heparinized whole blood after centrifugation at 1000×g for 20 min, except for those to be purified with spin-columns, which were isolated after isopycnic centrifugation as described in Iqbal, Z., and Y. Rikihisa. 1994. Application of the polymerase chain reaction for the detection of *Ehrlichia canis* in tissues of dogs. Vet. Microbiol. 42:281–7. All DNA isolations with commercial kits were performed in strict accordance to the manufacturer's instructions. DNAzol and DNAzol-BD isolations were performed in the presence of polyacryl carrier (Molecular Research Center) as recommended by the manufacturer.

The remaining method was a modification of a protocol that was previously described in Stich, R. Wet al. 1991. Preliminary development of a polymerase chain reaction assay for *Anaplasma marginale* in ticks. Biotechnol. Techniq. 5:269–274.; and Stich, R. W., et al 1993. Detection of *Anaplasma marginale* (Rickettsiales: Anaplasmataceae) in secretagogue-induced oral secretions of *Dermacentor andersoni* (Acari: Ixodidae) with the polymerase chain reaction J. Med. Entomol. 30:789–94. Briefly, the buffy coats were removed from whole blood and transferred to a 1.5 ml microfuge tube. Erythrocytes remaining in the buffy coat were lysed with two volumes of TE (10 mM Tris HCI, pH 8.0, 1 mM EDTA), and the hemoglobin was removed by washing pelleted cells (13,000×g for 1 min) three times in TE. The final cell suspension was in 400 μl of RPMI 1640 containing 100 μg/ml proteinase K and 0.45% (v/v) NP-40 and 0.45% (v/v) Tween-20, and the protein was digested for 1–2 hr at 55° C. Digests were extracted one time each with equal volumes of buffer-saturated phenol (pH>7.5) (Life Technologies), phenol/chloroform/isoamyl alcohol (25:24:1), and chloroform/isoamyl alcohol (24:1). DNA was precipitated by adding 1/10 volume of 3 M sodium acetate and 2.5 volumes of absolute ethanol (−20° C.) and stored overnight at −20° C. The DNA samples were centrifuged at 13,000×g for 20 min at 4° C., allowed to air dry in a sterile, bleach-treated cabinet and resuspended in 25 μl of HPLC grade $H_2O$. The samples containing *E. canis* DNA were diluted empirically throughout the optimization process.

B. Nested PCR

The primers used in the first PCR reaction is set 12 shown in Table 1 above. The primers used in the second PCT reaction is set 1 shown in Table 1 above. PCR was performed with a Perkin-Elmer 2400 thermal cycler. Master mixes, made with the PE Biosystems Reagents (Foster City, Calif.), were divided into 50 or 25 μl final reaction volumes containing PCR Gold buffer, 0.8 mM dNTP mix and specified amounts of $MgCl_2$, primers, Amplitaq-Gold DNA Polymerase and 10% (v/v) template. The reaction profile, except for stated exceptions, consisted of 95° C. for 10 min followed by 35 cycles of 94° C. for 1.0 min, 60° C. for 0.5 min, and 72° C. for 0.5 min followed final extension at 72° C. for 7.0 min.

The following PCR parameters were progressively optimized: (1) annealing temperature (37°, 50°, 55°, 60°, 65° and 70° C. with 1.5 mM $MgCl_2$, 0.5 μM primers and 0.025 U/μl Amplitaq-Gold), (2) $MgCl_2$ concentration (1.0–4.0 mM $MgCl_2$ in 0.5 mM increments), (3) primer concentration (0.1–1.0 μM in 0.1 μM increments), (4) Amplitaq-Gold concentration (0.01–0.1 U/μl in 0.01 U/μl increments) and (5) cycle number (25–65 cycles in 5 cycle increments).

C. Analysis of PCR Products

PCR product (20 μl) was added to 5 μl of loading buffer (40% (w/v) sucrose, 89 mM Tris, 89 mM boric acid, 2 mM EDTA) and electrophoresed on a 1.5% (w/v) agarose gel with 0.5 μg/ml ethidium bromide in 1×TBE (89 mM Tris, 89 mM boric acid, 2 mM EDTA) at 60–80 V for 1–1.5 hr. A 100 bp ladder (Life Technologies, Rockville, Md.) was used as the molecular weight standard. DNA bands were visualized with ultraviolet light and documented using an Alpha Innotech 2000 gel imaging system.

RESULTS

Amplification of the 200 bp Target Sequence by Nested PCR of *E. canis*-infected Peripheral Blood from Dogs with Acute Experimental CME A 200 bp band was amplified from DNA prepared from blood samples collected from three dogs during acute or chronic experimental CME (FIG. 1). This band was not observed from blood collected prior to infection of the two dogs assayed during acute CME. The DNA sequence of this amplicon was found to be identical to the 200 bp p30 target sequence and the reverse complement of ECAR1583A (FIG. 2).

Optimum Conditions for Isolating DNA from Blood Samples

Figure 3:
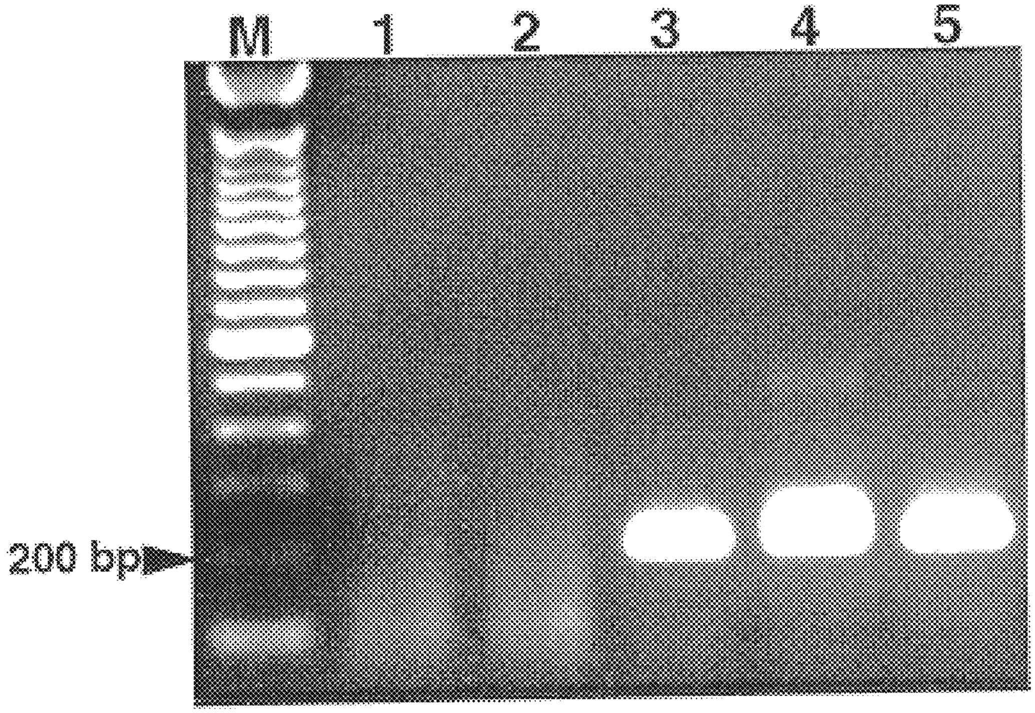
FIG. 3 shows the results of a PCR assay of peripheral blood from dogs during acute and chronic experimental CME. Three dogs were tested with the nested p30-based PCR described in the text. Buffy coat DNA preparations were assayed from two dogs prior to (lanes 1 and 3) and 21 d after (Lanes 3 and 4) inoculation with *E. canis* Ebony isolate-infected blood from an experimentally infected dog. The third dog (lane 5) was from the experimentally infected donor blood. The molecular size standard (M) is a 100 bp ladder (Life Technologies).
Figure 5:
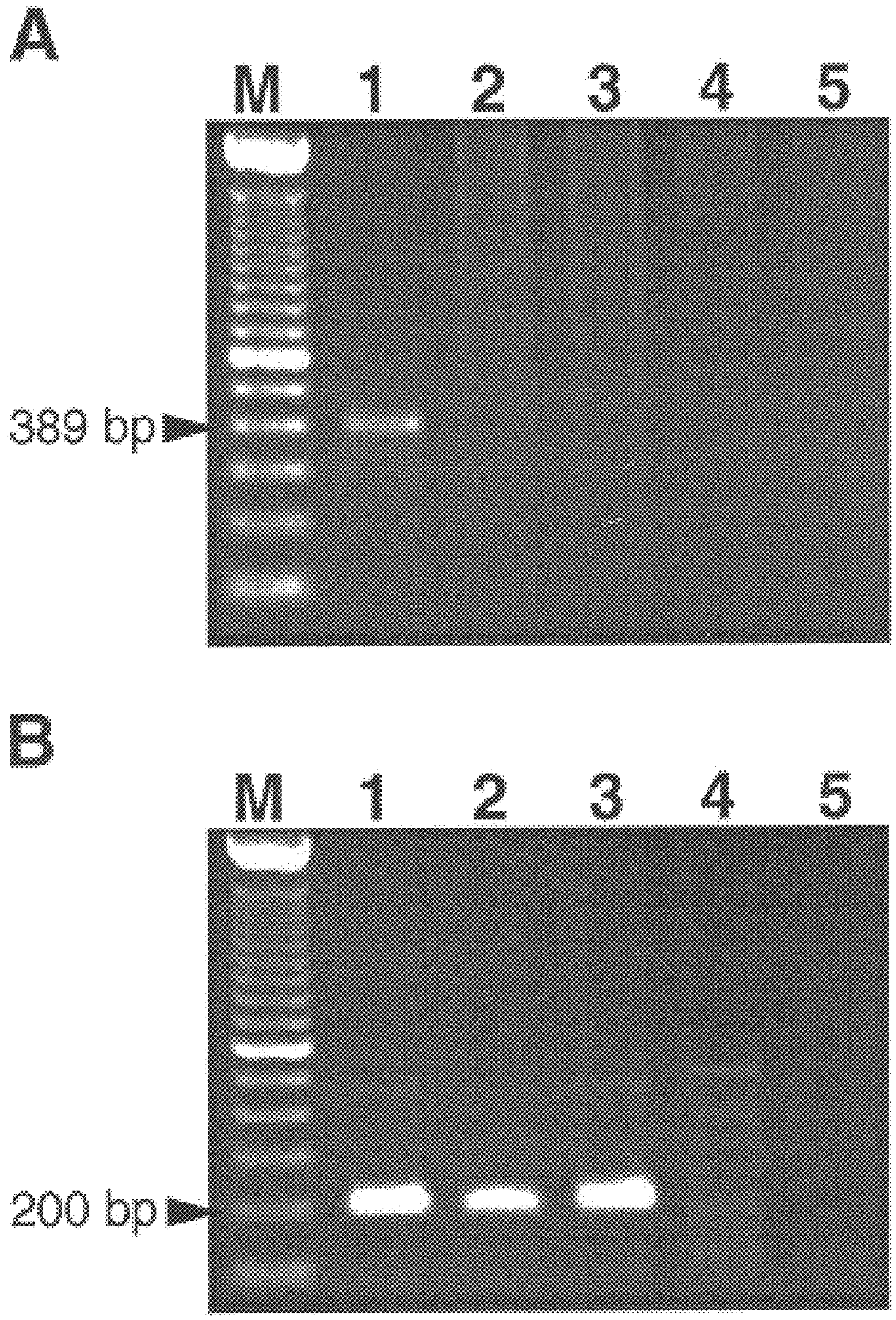
FIG. 5. shows: Sensitivity of the p30-based nested PCR assay. The 16S rDNA (panel A) and p30 (panel B) PCR assays were compared to determine relative sensitivities. Buffy coat DNA was isolated from an *E. canis* carrier dog and subjected to a dilution series for simultaneous amplification with the two assays. Lanes 1–5, respectively, are assays of the template dilutions of $1\times10^0$, $10^{-1}$, $10^{-2}$, $10^{-3}$ and $10^{-4}$ for both panels.
Figure 6:
FIG. 6. shows: Specificity of the p30-based nested PCR assay. Lane 1 is the template-free control, lanes 2–3 represent amplification of 50 ng of *E. canis* Ebony and Oklahoma isolates, respectively, and lanes 4–6 represent assay of 50 ng of DNA isolated from *E. chaffeensis,* HGE agent and *E. muris,* respectively. The 100 bp ladder (M) serves as the molecular size standard.
Figure 7:
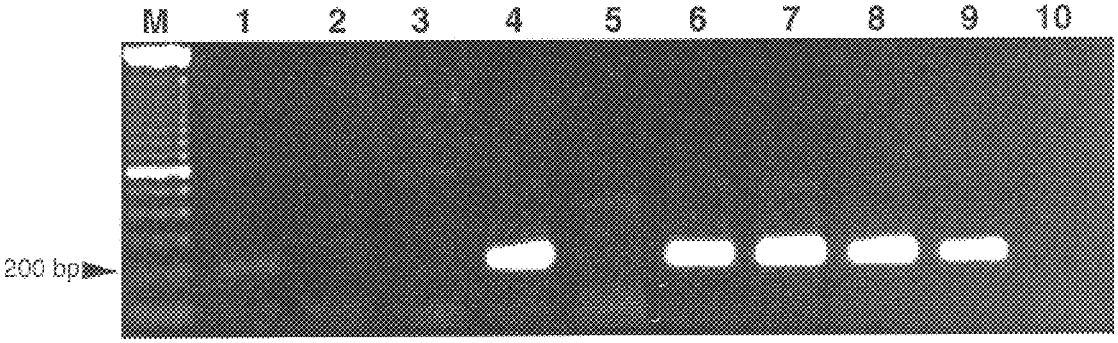
FIG. 7. shows: Preparation of blood samples for the p30-based nested PCR assay. Blood was collected with heparin from an *E. canis*-infected carrier dog, divided into 0.5 ml aliquots and subjected to different preparation procedures performed in duplicate as described in the text. Samples assayed with the nested p30-based PCR included buffy coats treated with DNAzol (Lanes 1 and 2), buffy coats treated with DNAzol BD (Lanes 3 and 4), whole blood treated with DNAzol BD (Lanes 5 and 6), buffy coats subjected to proteinase K digestion followed by phenol extraction and ethanol precipitation (Lanes 7 and 8) and DNA extracted from PBMC with Qiagen spin columns (Lanes 9 and 10). A 100 bp DNA ladder (M) was used as a molecular size standard.
Figure 8:
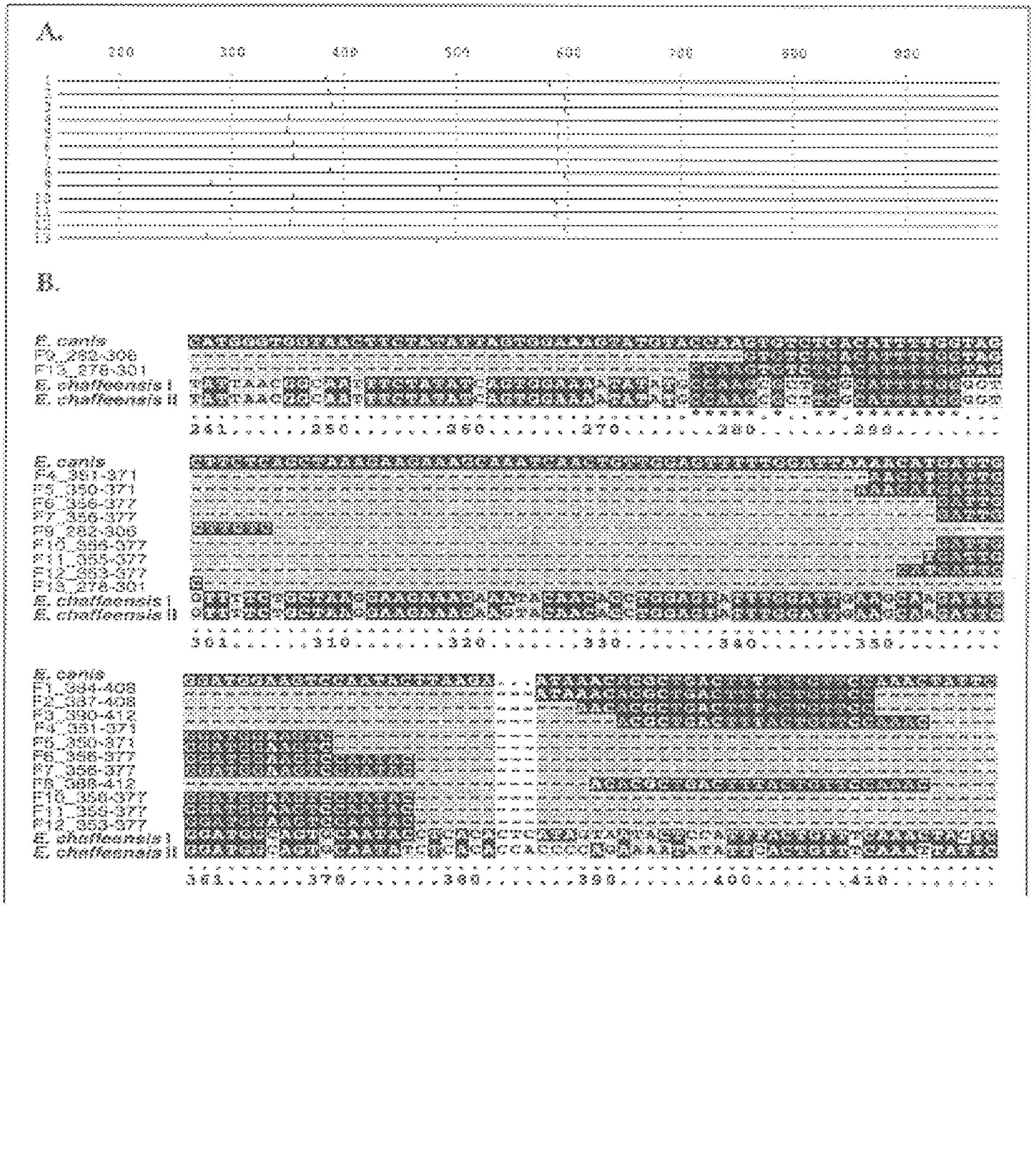
FIG. 8. Analysis of oligonucleotide primer sets derived from the *E. canis* p30 gene sequence. In the primer site plot (A), the horizontal lines represent the portion of the p30 open reading frame analyzed for optimal primer pairs. Each horizontal line represents the p30 ORF; vertical bars above the line represent the location of forward primers and vertical bars below each line represent reverse primers. The truncated multiple sequence (B) demonstrates similarity between the sequences of the forward primers and the *E. chaffeensis* p28 sequence clusters I (nucleotides 93–272 of SEQ ID NO. 48), II (nucleotides 93–272 of SEQ ID NO. 48) and III to the *E. canis* p30 sequence (nucleotides 241–417 of SEQ ID NO. 47). Letters surrounded by a black box represent bases identical to the *E. canis* sequence. Gray letters surrounded by a black box represent bases identical to *E. canis* and all three *E. chaffeensis* gene clusters. The same analysis was performed for reverse primers. The percent identical bases between the different primers and the *E. chaffeensis* cluster sequences were determined and are displayed in Table 1. Other sequences and their SEQ ID NOs. are as follows: F1_384–408, SEQ ID NO. 6; F2_387–408, SEQ ID NO. 8; F3_390–412, SEQ ID NO. 10; F4_351–371, SEQ ID NO. 11; F5_350–371, SEQ ID NO. 13; F6_356–377, SEQ ID NO. 15; F7_356–377, SEQ. ID NO. 15; F8_388–412, SEQ ID NO. 16; F9_282–306, SEQ ID NO. 18; F10_ 356–377, SEQ ID NO. 15; F11_355–377, SEQ ID NO. 21; F12_353–377, SEQ ID NO. 23; F13_ 278–301, SEQ ID NO. 24.
Figure 9:
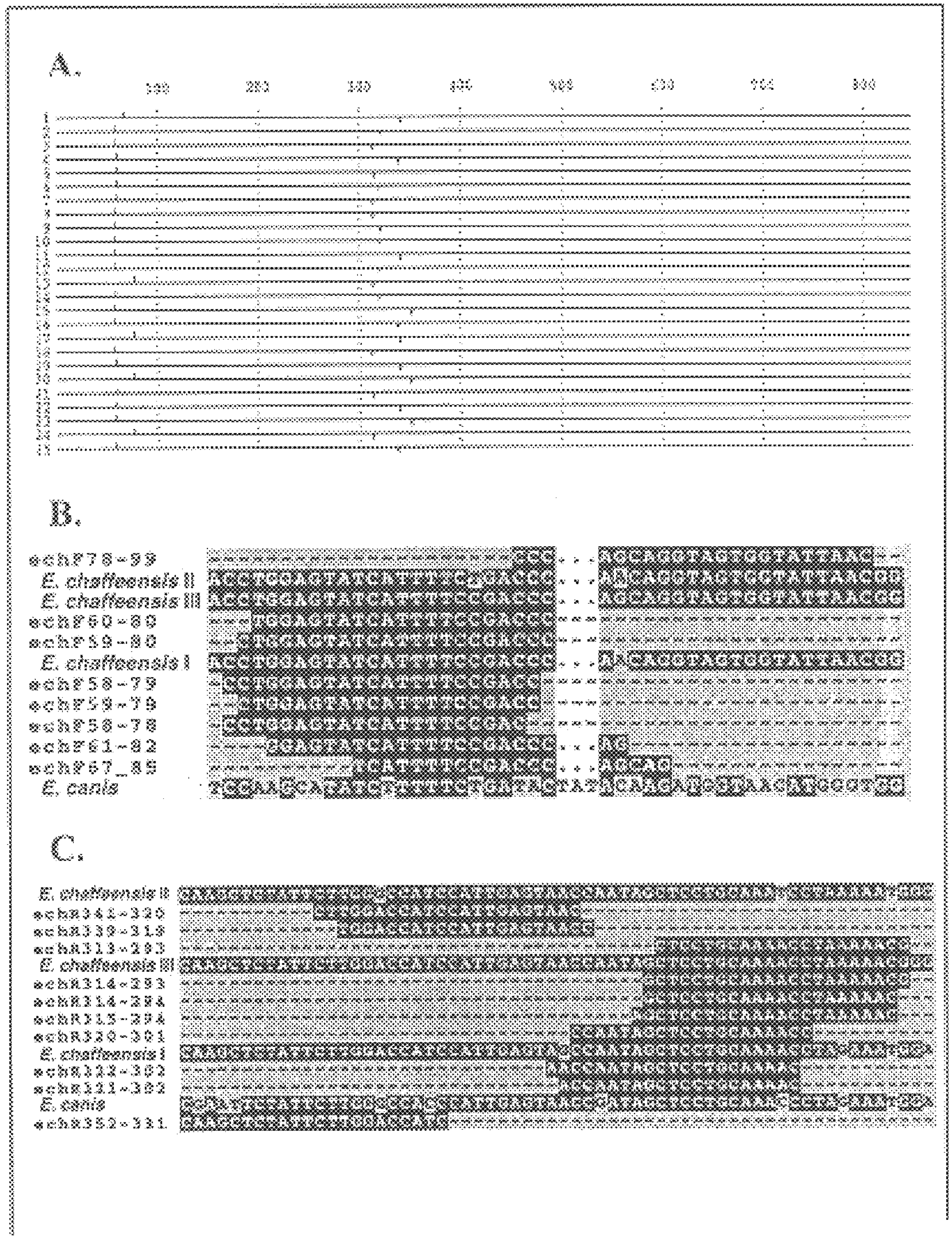
FIG. 9. Analysis of oligonucleotide primer sets derived from the *E. chaffeensis* p28 consensus sequence. The primer site plot (A) represents the location of forward and reverse primers within p28; vertical bars above the line represent the location of forward primers and vertical bars below each line represent reverse primers. The truncated multiple sequence alignments demonstrate identity between the sequences of the forward (B) and reverse (C) primers. Gray letters surrounded by a black box represent bases identical to *E. canis* and all three *E. chaffeensis* gene clusters. The percent identical bases between the different primers and the *E. canis* sequences were determined and are displayed in Table 5. In (B), sequences and their SEQ ID NOs. are as follows: *E. chaffeensis* I, II, and III, nucleotides 57 to 101 of SEQ ID NO. 48; echF58–78, nucleotides 58–78 of SEQ ID NO. 48.

Several approaches to blood preparation for PCR assay were compared with duplicate samples in two trials. Venous blood was collected with heparin from an experimentally infected *E. canis* carrier, equal aliquots that were subjected to different protocols for the preparation of template for PCR. Inhibition of PCR by hemoglobin is well known, thus removing hemoglobin from the blood sample is a major concern of any procedure used to assay these samples with PCR. Commercially available chemical and spin column kits for DNA isolation did provide some positive results with buffy coat and whole blood samples, but these treatments were inconsistent, failing to result in amplification of DNA in both duplicates of both trials. However, buffy coat isolation followed by lysing residual erythrocytes, removal of hemoglobin, protein digestion, protein extraction and DNA precipitation was the only procedure that resulted in amplification of the 200 bp target in both duplicates of both trials (FIG. 5). Moreover, this method has been used to detect *E. canis* in peripheral blood of a carrier dog for over one year (data not shown).

Optimization of the p30-based PCR Assay for *E. canis*

Initial optimization experiments with primer set 2 resulted in the amplification of multiple bands, thus this primer set is less preferred. The remaining assays employed primer sets 1 and 12. For the primary reaction with set 12, optimum PCR conditions were determined to be 1.5 mM $MgCl_2$, 0.2 μM of each primer, 0.04 units/μl of Amplitaq-Gold and, after enzyme activation at 95° C. for 10 min, 55 cycles with 94, 65 and 72° C. denaturation, annealing and extension temperatures for 30 sec each. For the secondary or nested PCR with internal primer set 1, optimum reaction conditions were determined to be 2.5 mM $MgCl_2$, 0.5 μM of each primer, 0.03 units/μl of Amplitaq-Gold, 10% (vol/vol) of the appropriate primary reaction with primer set 12 and 40 cycles with 94, 60 and 72° C. denaturation, annealing and extension temperatures for 30 sec each.

To confirm that the 200 bp amplicon associated with *E. canis* infection originated from the target DNA sequence, several p30-based nested PCR assays of buffy coat DNA from an *E. canis*-infected dog were pooled and the amplicons isolated with the QIAquik PCR Purification Kit (Qiagen, Valencia, Calif.) according to the manufacturer's instructions. The purified amplicon was submitted to The Ohio State University Neurobiotechnology DNA Sequencing Facility for cycle sequencing in the presence of the primer, ECAF1384S.

The optimum number of cycles for both reactions, particularly the primary reaction, were somewhat greater than expected. One explanation for this may be the enzyme used, Amplitaq-Gold, which requires activation at 95° C. for 10 min prior to the amplification cycles. It is possible that a portion of this enzyme remains inactive until the amplification cycles are underway; thus additional active enzyme becomes available in the course of the reaction, increasing the number of cycles required for optimal PCR.

Specificity and Sensitivity

The sensitivity of this p30-based assay was compared to that of the previously reported 16S rDNA-based assay as described in Wen, B., Y. Rikihisa, J. M. Mott, R. Greene, H. Y. Kim, N. Zhi, G. C. Couto, A. Unver, and R. Bartsch. 1997. Comparison of nested PCR with immunofluorescent-antibody assay for detection of *Ehrlichia canis* infection in dogs treated with doxycycline. J. Clin. Microbiol. 35:1852–5.The buffy coat fraction was removed from 5 ml of heparinized blood from an experimentally infected dog during acute CME, and subjected to DNA isolation with DNAzol (Molecular Research Center) according to the manufacturer's instructions. A tenfold dilution series of the buffy coat DNA was then tested with both the p30- and the 16S rDNA-based PCR assays.

Specificity of the p30-based assay was tested by attempts to amplify 50 ng samples of DNA isolated from *E. muris, E. chaffeensis* and HGE agent in experimentally infected host cells. DNA. *E. chaffeensis* and *E. muris* are the two known species most closely related to *E. canis* (based on 16S rDNA sequence homology) Faint bands at sizes other than that of the target sequence were occasionally observed, indicating that similar omp-1 sequences may be amplified under these conditions, but the robust 200 bp band was only observed with *E. canis* template.

Example 2

E. chaffeensis p28 ORF sequences were compared to identify prospective oligonucleotide primer sequences for a PCR assay. Design of the primers for this PCR assay was similar to that described for E. canis, except that identities of these primers to the three clusters of p28 sequences among the E chaffeensis isolates were also considered by dividing the product of the annealing and E. canis identity scores by the mean of the three E.chaffeensis cluster identity scores. Primers were designed from the E. chaffeensis Arkansas isolate p28 sequence. These primer sequences were aligned with the homologous portions of the E. canis p30 geme and the three p28 clusters and the identity of these sequences determined Total annealing scores, identity to the different p28 clusters and identity to p30 were then used to rank these primer sets. A second approach to primer design involved the design of primers to the consensus sequence of all three E. chaffeensis p28 clusters through less stringent annealing score parameters. These primers, which are shown in Table 3 above are expected to be universal for all five E. chaffeensis isolates that composed these three clusters.

Primers for E. chaffeensis were designed with the Wisconsin Package (GCG) Version 10 software suite (Madison, Wis.). This was accomplished with a multiple sequence alignment of the target template from isolates representing all three clusters of E. chaffeensis of and the E. canis p30 sequence. Initially optimal primer sequences could not be obtained from the consensus of all three p28 sequences, thus primers were designed from the E. chaffeensis Arkansas isolate p28 sequence since this is the isolate to be used in the proposed investigation. Twenty-five sets of primers were then identified. These primer sequences were aligned with the homologous portions of p30 and the three p28 clusters and the identity of these sequences determined. Total annealing scores, identity to the different p28 clusters and identity to p30 were then used to rank these primer sets. Three primer sets were chosen for development of a p28-based assay by virtue of their overall rank and relative positions flanking or internal to other primer sets for nested PCR and found to amplify E. chaffeensis DNA from infected canine cells. Two of the E. chaffeensis Arkansas isolate-specific primer sets were optimized and used as a nested PCR assay to detect the pathogen in intrastadially infected male ticks of four species known to parasitize dogs.

TABLE 4

Ranks of E. chaffeensis p28 primer sets with predicted annealing and specificity values.[a]

| Set | Primers Fwd. | Primers Rev. | Aneal- ing Score | Cluster I Fwd. | Cluster I Rev. | Cluster II Fwd. | Cluster II Rev. | Cluster III Fwd. | Cluster III Rev. | Mean | E. canis Fwd. | E. canis Rev. | Mean | Rank |
|---|---|---|---|---|---|---|---|---|---|---|---|---|---|---|
| 1[b] | 67–85 | 341–320 | 55 | 1.0 | 1.0 | 0.90 | 0.95 | 1.0 | 1.0 | 0.98 | 0.68 | 0.91 | 0.80 | 8 |
| 2 | 58–78 | 321–302 | 58 | 1.0 | 0.95 | 0.95 | 0.95 | 1.0 | 1.0 | 0.98 | 0.57 | 0.90 | 0.74 | 7 |
| 3 | 58–78 | 314–294 | 58 | 1.0 | 0.90 | 0.95 | 0.90 | 1.0 | 1.0 | 0.96 | 0.57 | 0.86 | 0.72 | 5 |
| 4 | 61–82 | 339–319 | 58 | 1.0 | 0.90 | 0.91 | 0.95 | 1.0 | 1.0 | 0.96 | 0.64 | 0.86 | 0.75 | 10 |
| 5 | 61–82 | 315–294 | 59 | 1.0 | 0.91 | 0.91 | 0.91 | 1.0 | 1.0 | 0.96 | 0.64 | 0.86 | 0.75 | 15 |
| 6 | 61–82 | 320–301 | 59 | 1.0 | 1.0 | 0.91 | 0.95 | 1.0 | 1.0 | 0.98 | 0.64 | 0.90 | 0.77 | 16 |
| 7 | 60–80 | 314–294 | 60 | 1.0 | 0.90 | 0.95 | 0.90 | 1.0 | 1.0 | 0.96 | 0.62 | 0.86 | 0.74 | 13 |
| 8 | 59–79 | 314–294 | 60 | 1.0 | 0.90 | 0.95 | 0.90 | 1.0 | 1.0 | 0.96 | 0.62 | 0.86 | 0.74 | 14 |
| 9 | 58–79 | 322–302 | 60 | 1.0 | 0.95 | 0.95 | 0.95 | 1.0 | 1.0 | 0.98 | 0.59 | 0.90 | 0.75 | 11 |
| 10 | 58–78 | 320–301 | 60 | 1.0 | 1.0 | 0.95 | 0.95 | 1.0 | 1.0 | 0.98 | 0.57 | 0.90 | 0.74 | 9 |
| *11[b] | 58–78 | 341–320 | 61 | 1.0 | 1.0 | 0.95 | 0.95 | 1.0 | 1.0 | 0.98 | 0.57 | 0.91 | 0.74 | 12 |
| 12 | 59–79 | 320–301 | 62 | 1.0 | 1.0 | 0.95 | 0.95 | 1.0 | 1.0 | 0.98 | 0.62 | 0.90 | 0.76 | 19 |
| 13[b'] | 78–99 | 314–294 | 62 | 1.0 | 0.90 | 0.95 | 0.90 | 1.0 | 1.0 | 0.96 | 0.41 | 0.86 | 0.64 | 2 |
| 14 | 59–80 | 320–301 | 62 | 1.0 | 1.0 | 0.95 | 0.95 | 1.0 | 1.0 | 0.98 | 0.64 | 0.90 | 0.77 | 20 |
| 15 | 58–78 | 352–331 | 62 | 1.0 | 1.0 | 0.95 | 0.95 | 1.0 | 1.0 | 0.98 | 0.57 | 0.77 | 0.67 | 3 |
| 16 | 58–78 | 339–319 | 64 | 1.0 | 0.90 | 0.95 | 0.95 | 1.0 | 1.0 | 0.97 | 0.57 | 0.86 | 0.72 | 18 |
| 17 | 78–99 | 341–320 | 64 | 1.0 | 1.0 | 0.95 | 0.95 | 1.0 | 1.0 | 0.98 | 0.41 | 0.91 | 0.66 | 4 |
| 18 | 58–78 | 313–293 | 65 | 1.0 | 0.95 | 0.95 | 0.90 | 1.0 | 1.0 | 0.97 | 0.57 | 0.95 | 0.76 | 25 |
| 19 | 60–80 | 341–320 | 64 | 1.0 | 1.0 | 0.95 | 0.95 | 1.0 | 1.0 | 0.98 | 0.62 | 0.91 | 0.77 | 21 |
| 20 | 78–99 | 352–331 | 65 | 1.0 | 1.0 | 0.95 | 0.95 | 1.0 | 1.0 | 0.98 | 0.41 | 0.77 | 0.59 | 1 |
| 21 | 61–82 | 314–293 | 65 | 1.0 | 0.91 | 0.91 | 0.91 | 1.0 | 1.0 | 0.96 | 0.64 | 0.86 | 0.75 | 24 |
| 22 | 59–79 | 341–320 | 65 | 1.0 | 1.0 | 0.95 | 0.95 | 1.0 | 1.0 | 0.98 | 0.62 | 0.91 | 0.77 | 23 |
| 23 | 59–80 | 352–331 | 66 | 1.0 | 1.0 | 0.95 | 0.95 | 1.0 | 1.0 | 0.98 | 0.64 | 0.77 | 0.71 | 17 |
| 24[b'] | 78–99 | 314–293 | 66 | 1.0 | 0.91 | 0.95 | 0.91 | 1.0 | 1.0 | 0.96 | 0.41 | 0.86 | 0.64 | 6 |
| 25 | 60–80 | 339–319 | 66 | 1.0 | 0.90 | 0.95 | 0.95 | 1.0 | 1.0 | 0.97 | 0.62 | 0.86 | 0.74 | 22 |

[a]All values determined as described for Table 1, except for Rank, which was determined by the product of annealing score and mean E. canis identity score, divided by mean E. chaffeensis annealing score; lower values have higher rank.
[b,b']Nested primer sets.
*Primer sets chosen for optimization.

Primers derived from both approaches were chosen for use in a p28-based assay by virtue of their overall rank and relative positions flanking or internal to other primer sets for nested PCR. These candidate primer were synthesized and they were all tested with 50 ng of DNA from E. chaffeensis-infected DH82 cells and Life Technologies reagents at concentrations of 1×PCR buffer, 1.5 mM $MgCl_2$, 0.5 µM of each primer and 0.025 U/µl Platinum Taq DNA Polymerase at an initial incubation period at 94° C. for 2 min followed by 25 cycles of 94° C. for 30 sec, 50° C. for 30 sec and 72° C. for 1 min 7 min final extension step at 72° C. Each primer set tested amplified a clean, robust amplicon of the expected size under unoptimized conditions. Primer sets F58/R341 and F78/R314 were chosen first for optimization due to the more stringent parameters used for their selection.

Optimum parameters for primer sets F58/R341 and F78/R314 were then used to assay canine and tick host samples. Dog number 146 was inoculated iv. with DH82 cells that were infected in vitro with *E. chaffeensis* (Arkansas isolate). Once the dog was PCR-positive by the 16S rDNA-based PCR assay and seroconverted, it was infested with 150 adult males of *A. americanum,* and 10 each of *A. maculatum, D. variabilis* and *R. sanguineus.* These ticks were allowed to simultaneously acquisition feed seven days prior to their removal and incubation in a humidity chamber for another 10 days. The held ticks were then placed at 37° C. at 100% rh for 80 hr before they were aseptically bisected and digested with proteinase K in the presence of nonionic detergents. These ticks (2.5 $\mu$l) were then assayed with *E. chaffeensis* p28-specific nested primer sets $11_A$ (F58/R341) and $13_A$ (F78/R314).

Samples from each tick species fed tested PCR-positive at a frequency of 20–40% with the nested assay. These results are the first to our knowledge to demonstrate detection of *E. chaffeensis* in experimentally infected ticks, only the second time to detect *E. chaffeensis* in individual ticks and the first detection of this pathogen in *A. maculatum* or *R. sanguineus.*

Further sequence analysis with less stringent criteria did reveal 20 primer sequences complementary to the p28 consensus sequence of all three clusters. Two sets of the consensus primers (See * in Table 5 below) were also tested and found to amplify robust amplicons from *E. chaffeensis* DNA.

TABLE 5

Ranks of universal *E. chaffeensis* p28 primer sets with predicted values.

| | Primers | | Aneal -ing | Identity Scores to *E. canis* | | | |
|---|---|---|---|---|---|---|---|
| Set | Fwd. | Rev. | Score | Fwd. | Rev. | Mean | Rank |
| *1 | 84–101 | 360–341 | 57 | 0.5 | 0.8 | 0.65 | 1 |
| 2 | 84–101 | 365–346 | 57 | 0.5 | 0.8 | 0.65 | 1 |
| *3 | 50–68 | 669–649 | 61 | 0.58 | 0.67 | 0.62 | 3 |
| 4 | 83–100 | 364–346 | 63 | 0.44 | 0.79 | 0.62 | 5 |
| 5 | 83–100 | 359–341 | 63 | 0.44 | 0.79 | 0.62 | 5 |
| 6 | 50–68 | 669–650 | 63 | 0.58 | 0.65 | 0.61 | 4 |
| 7 | 55–74 | 670–650 | 64 | 0.65 | 0.67 | 0.66 | 7 |
| 8 | 45–62 | 359–341 | 65 | 0.61 | 0.79 | 0.70 | 10 |
| 9 | 15–32 | 364–346 | 66 | 0.78 | 0.79 | 0.78 | 19 |
| 10 | 15–32 | 359–341 | 66 | 0.78 | 0.79 | 0.78 | 19 |
| 11 | 50–74 | 662–637 | 67 | 0.64 | 0.73 | 0.69 | 11 |
| 12 | 50–68 | 662–641 | 67 | 0.58 | 0.68 | 0.63 | 8 |
| 13 | 45–62 | 365–348 | 68 | 0.61 | 0.78 | 0.69 | 13 |
| 14 | 45–62 | 364–346 | 69 | 0.61 | 0.79 | 0.70 | 15 |
| 15 | 51–74 | 670–645 | 69 | 0.67 | 0.58 | 0.62 | 9 |
| 16 | 53–74 | 670–649 | 71 | 0.69 | 0.64 | 0.66 | 12 |
| 17 | 53–74 | 662–641 | 71 | 0.67 | 0.72 | 0.69 | 17 |
| 18 | 57–74 | 674–657 | 73 | 0.67 | 0.72 | 0.69 | 14 |
| 19 | 50–68 | 673–656 | 73 | 0.58 | 0.72 | 0.65 | 14 |
| 20 | 55–74 | 673–656 | 75 | 0.65 | 0.72 | 0.69 | 18 |

What is claimed is:

1. A method for detecting *E. canis* in a sample obtained from an animal, comprising (a) providing a primer set comprising:

(i) a forward primer of from 15 to 35 nucleotides in length, said forward primer comprising a sequence which is the complement of a consecutive sequence within the following sequence: CCA AGTGTCTCAC ATTTTGGTAG CTTCTCAGCT AAAGAAGAAA GCAAATCAAC TGTTGGAGTTTTTGGATTAA AACATGATTG GGATGGAAGT CCAATACTTA AGAATAAACA CGCTGACTTTACTGTTCCAA AC SEQ ID NO.1, and (ii) a reverse primer of from 15 to 35 nucleotides in length, said reverse primer comprising a sequence which is complementary to the inverse complement of a consecutive sequence within the following sequence: GTTACT CAATGGGTGG CCCAAGAATA GAATTCGAAA TATCTTATGA AGCATTCGAC GTAAAAAGTC CTAATATCAA TTATCAAAAT GACGCGCACA GGTACTGCGC TCTATCTCAT CACACATCGG CAGCCAT, SEQ ID NO.2;

(b) amplifying DNA in the sample with the said primer set and a polymerase chain reaction, and (c) determining the length or sequence of the PCR products of step (b), wherein the presence of a PCR product having a length or sequence which corresponds to the length or sequence, respectively, of that region of the *E. canis* p30 gene which is located between the regions to which the forward primer and the reverse primer bind is indicative of the presence of *E. canis* in the sample.

2. The method of claim 1 wherein the consecutive sequence is at least 14 nucleotides in length.

3. The method of claim 1 wherein the forward primer and the reverse primer, respectively, comprise one of the following pairs of sequences:

PAIR 1: ATAAACACGCTGACTTTACTGTTCC, SEQ ID NO.6, GTGATGAGATAGAGCGCAGTACC, SEQ ID NO. 7;

PAIR 2: AACACGCTGACTTTACTGTTCC, SEQ ID NO. 8, ATGGCTGCCGATGTGTGATG, SEQ ID NO. 9;

PAIR 3: ACGCTGACTTTACTGTTCCAAAC, SEQ ID NO. 10, ATGGCTGCCGATGTGTGATG, SEQ ID NO. 9;

PAIR 4: AACATGATTGGGATGGAAGTC, SEQ ID NO. 11, GCCGATGTGTGATGAGATAG, SEQ ID NO. 12;

PAIR 5: AAACATGATTGGGATGGAAGTC, SEQ ID NO.13, GCCGATGTGTGATGAGATAGAG, SEQ ID NO. 14;

PAIR 6: GATTGGGATGGAAGTCCAATAC, SEQ ID NO. 15, GCCGATGTGTGATGAGATAG, SEQ ID NO.11;

PAIR 7: GATTGGGATGGAAGTCCAATAC, SEQ ID NO. 15, GCCGATGTGTGATGAGATAGAG, SEQ BD NO. 14;

PAIR 8: ACACGCTGACTTTACTGTTCCAAAC, SEQ ID NO. 16, ATGGCTGCCGATGTGTGATGAG, SEQ ID NO. 17;

PAIR 9: GTGTCTCACATTTTGGTAGCTTCTC, SEQ ID NO. 18, CTTGGGCCACCCATTGAGTAAC, SEQ ID NO. 19;

PAIR 10: GATTGGGATGGAAGTCCAATAC, SEQ ID NO. 15, CGATGTGTGATGAGATAGAGC, SEQ ID NO. 20;

PAIR 11: TGATTGGGATGGAAGTCCAATAC, SEQ ID NO. 21, CGATGTGTGATGAGATAGAGCG, SEQ ID NO. 22;

PAIR 12: CATGATTGGGATGGAAGTCCAATAC, SEQ ID NO. 23, ATGGCTGCCGATGTGTGATG, SEQ ID NO. 9;

PAIR 13: CCAAGTGTCTCACATTTTGGTAGC, SEQ ID NO. 24, TGGGCCACCCATTGAGTAAC, SEQ ID NO. 25.

4. The method of claim 3 wherein the primer set is pair 12.

5. The method of claim 3 wherein the primer set is pair 1.

6. A method for detecting *E. canis* in a sample obtained from an animal, comprising (a) providing a first primer set comprising:

(i) a forward primer of from 15 to 35 nucleotides in length, said forward primer comprising a sequence which is the complement of a consecutive sequence within the following sequence: CCA AGTGTCTCAC ATTTTGGTAG CTTCTCAGCT AAAGAAGAAA GCAAATCAAC TGTTGGAGTTTTTGGATTAA AACATGATTG GGATGGAAGT CCAATACTTA AGAATAAACA CGCTGACTTTACTGTTCCAA AC, SEQ ID NO. 1, and (ii) a reverse primer of from 15 to 35 nucleotides in length, said reverse primer comprising a sequence which is complementary to the inverse complement of a consecutive sequence within the following sequence: GTTACT CAATGGGTGG CCCAAGAATA GAATTCGAAA TATCTTATGA AGCATTCGAC GTAAAAAGTC CTAATATCAA TTATCAAAAT GACGCGCACA GGTACTGCGC TCTATCTCAT CACACATCGG CAGCCAT, SEQ ID NO.2;

(b) amplifying DNA in the sample with the said primer set and a polymerase chain reaction to provide a pool of PCR products, (c) amplifying the products of step (b) using a polymerase chain reaction and a second primer set comprising:

(i) a forward primer of from 15 to 35 nucleotides in length, said forward primer comprising a sequence which is the complement of a consecutive sequence within the following sequence: CCA AGTGTCTCAC ATTTTGGTAG CTTCTCAGCT AAAGAAGAAA GCAAATCAAC TGTTGGAGTTTTTGGATTAA AACATGATTG GGATGGAAGT CCAATACTTA AGAATAAACA CGCTGACTTTACTGTTCCAA AC, SEQ ID NO.1, and (ii) a reverse primer of from 15 to 35 nucleotides in length, said reverse primer comprising a sequence which is complementary to the inverse complement of a consecutive sequence within the following sequence: GTTACT CAATGGGTGG CCCAAGAATA GAATTCGAAA TATCTTATGA AGCATTCGAC GTAAAAAGTC CTAATATCAA TTATCAAAAT GACGCGCACA GGTACTGCGC TCTATCTCAT CACACATCGG CAGCCAT, SEQ ID NO.2;

wherein one or both of the primers of the second primer set are internal to the primers of the first primer set; and (d) determining the length or sequence of the PCR products of step (c), wherein the presence of a PCR product having a length or sequence which corresponds to the length or sequence, respectively, of that region of the *E. canis* p30 gene which is located between the regions to which the forward primer of the second primer set and the reverse primer of the second primer set bind is indicative of the presence of *E. canis* in the sample.

7. A primer set for detecting *E. canis* in a sample, said primer set comprising:

(a) a forward primer of from 15 to 35 nucleotides in length, said forward primer comprising a sequence which is the complement of a consecutive sequence within the following sequence: CCA AGTGTCTCAC ATTTTGGTAG CTTCTCAGCT AAAGAAGAAA GCAAATCAAC TGTTGGAGTTTTTGGATTAA AACATGATTG GGATGGAAGT CCAATACTTA AGAATAAACA CGCTGACTTTACTGTTCCAA AC, SEQ ID NO.1, and (ii) a reverse primer of from 15 to 35 nucleotides in length, said reverse primer comprising a sequence which is complementary to the inverse complement of a consecutive sequence within the following sequence: GTTACT CAATGGGTGG CCCAAGAATA GAATTCGAAA TATCTTATGA AGCATTCGAC GTAAAAAGTC CTAATATCAA TTATCAAAAT GACGCGCACA GGTACTGCGC TCTATCTCAT CACACATCGG CAGCCAT, SEQ ID NO.2.

8. The primer set of claim 7 wherein forward primer and the reverse primer, respectively, comprise one of the following pairs of sequences:

PAIR 1: ATAAACACGCTGACTTTACTGTTCC, SEQ ID NO.6, GTGATGAGATAGAGCGCAGTACC, SEQ ID NO. 7;

PAIR 2 AACACGCTGACTTTACTGTTCC, SEQ ID NO. 8, ATGGCTGCCGATGTGTGATG, SEQ ID NO. 9;

PAIR 3: ACGCTGACTTTACTGTTCCAAAC, SEQ ID NO. 10, ATGGCTGCCGATGTGTGATG, SEQ ID NO. 9;

PAIR 4: AACATGATTGGGATGGAAGTC, SEQ ID NO. 11, GCCGATGTGTGATGAGATAG, SEQ ID NO. 12;

PAIR 5: AAACATGATTGGGATGGAAGTC, SEQ. ID NO.13, GCCGATGTGTGATGAGATAGAG, SEQ ID NO. 14;

PAIR 6: GATTGGGATGGAAGTCCAATAC, SEQ. ID. NO. 15, GCCGATGTGTGATGAGATAG, SEQ ID NO.11;

PAIR 7: GATTGGGATGGAAGTCCAATAC, SEQ ID NO. 15, GCCGATGTGTGATGAGATAGAG, SEQ ID NO. 14;

PAIR 8: ACACGCTGACTTTACTGTTCCAAAC, SEQ ID NO. 16, ATGGCTGCCGATGTGTGATGAG, SEQ ID NO. 17;

PAIR 9: GTGTCTCACATTTTGGTAGCTTCTC, SEQ ID NO. 18, CTTGGGCCACCCATTGAGTAAC, SEQ ID NO. 19;

PAIR 10: GATTGGGATGGAAGTCCAATAC, SEQ. ID. NO. 15, CGATGTGTGATGAGATAGAGC, SEQ ID NO. 20;

PAIR 11: TGATTGGGATGGAAGTCCAATAC, SEQ ID NO. 21, CGATGTGTGATGAGATAGAGCG, SEQ ID NO. 22;

PAIR 12: CATGATTGGGATGGAAGTCCAATAC, SEQ ID NO. 23, ATGGCTGCCGATGTGTGATG, SEQ ID NO. 9;

PAIR 13: CCAAGTGTCTCACATTTTGGTAGC, SEQ ID NO. 24, TGGGCCACCCATTGAGTAAC, SEQ ID NO. 25.

9. The primer set of claim 8 wherein the primer set comprises pair 1.

10. The primer set of claim 8 wherein the primer set comprises pair 12.

* * * * *

UNITED STATES PATENT AND TRADEMARK OFFICE

CERTIFICATE OF CORRECTION

PATENT NO. : 6,432,649 B1 
DATED : August 13, 2002
INVENTOR(S) : Roger William Stich and Yasuko Rikihisa It is certified that error appears in the above-identified patent and that said Letters Patent is hereby corrected as shown below:

<u>Column 5,</u>
Line 12, please delete "ecbR314-293" and insert -- echR314-293 --.
Line 17, please delete "ehbR321-302" and insert -- echR321-302 --.

<u>Column 46,</u>
Line 52, please delete "SEQ BD NO." and insert -- SEQ ID NO. --

Signed and Sealed this

Twenty-first Day of January, 2003

JAMES E. ROGAN
*Director of the United States Patent and Trademark Office*

SEQUENCE LISTING

```
<160> NUMBER OF SEQ ID NOS: 51

<210> SEQ ID NO 1
<211> LENGTH: 135
<212> TYPE: DNA
<213> ORGANISM: Artificial Sequence
<220> FEATURE:
<223> OTHER INFORMATION: synthetic sequence

<400> SEQUENCE: 1

ccaagtgtct cacattttgg tagcttctca gctaaagaag aaagcaaatc aactgttgga     60

gtttttggat taaaacatga ttgggatgga agtccaatac ttaagaataa acacgctgac    120

tttactgttc caaac                                                     135


<210> SEQ ID NO 2
<211> LENGTH: 133
<212> TYPE: DNA
<213> ORGANISM: Artificial Sequence
<220> FEATURE:
<223> OTHER INFORMATION: synthetic sequence

<400> SEQUENCE: 2

gttactcaat gggtggccca agaatagaat tcgaaatatc ttatgaagca ttcgacgtaa     60

aaagtcctaa tatcaattat caaaatgacg cgcacaggta ctgcgctcta tctcatcaca    120

catcggcagc cat                                                       133
```

-continued

<210> SEQ ID NO 3
<211> LENGTH: 87
<212> TYPE: DNA
<213> ORGANISM: Artificial Sequence
<220> FEATURE:
<223> OTHER INFORMATION: synthetic sequence

<400> SEQUENCE: 3
agttttcata acaagtgcat tgatatcact aatatcttct ctacctggag tatcattttc 60
cgacccaaca ggtagtggta ttaacgg 87

<210> SEQ ID NO 4
<211> LENGTH: 73
<212> TYPE: DNA
<213> ORGANISM: Artificial Sequence
<220> FEATURE:
<223> OTHER INFORMATION: synthetic sequence

<400> SEQUENCE: 4
catttctagg ttttgcagga gctattggct actcaatgga tggtccaaga atagagcttg 60
aagtatctta tga 73

<210> SEQ ID NO 5
<211> LENGTH: 38
<212> TYPE: DNA
<213> ORGANISM: Artificial Sequence
<220> FEATURE:
<223> OTHER INFORMATION: synthetic sequence

<400> SEQUENCE: 5
caaggaaagt taggtttaag ctactctata agcccaga 38

<210> SEQ ID NO 6
<211> LENGTH: 25
<212> TYPE: DNA
<213> ORGANISM: Artificial Sequence
<220> FEATURE:
<223> OTHER INFORMATION: synthetic sequence

<400> SEQUENCE: 6
ataaacacgc tgactttact gttcc 25

<210> SEQ ID NO 7
<211> LENGTH: 23
<212> TYPE: DNA
<213> ORGANISM: Artificial Sequence
<220> FEATURE:
<223> OTHER INFORMATION: synthetic sequence

<400> SEQUENCE: 7
gtgatgagat agagcgcagt acc 23

<210> SEQ ID NO 8
<211> LENGTH: 22
<212> TYPE: DNA
<213> ORGANISM: Artificial Sequence
<220> FEATURE:
<223> OTHER INFORMATION: synthetic sequence

<400> SEQUENCE: 8
aacacgctga ctttactgtt cc 22

<210> SEQ ID NO 9
<211> LENGTH: 20

-continued

<212> TYPE: DNA
<213> ORGANISM: Artificial Sequence
<220> FEATURE:
<223> OTHER INFORMATION: synthetic sequence

<400> SEQUENCE: 9
atggctgccg atgtgtgatg 20

<210> SEQ ID NO 10
<211> LENGTH: 23
<212> TYPE: DNA
<213> ORGANISM: Artificial Sequence
<220> FEATURE:
<223> OTHER INFORMATION: synthetic sequence

<400> SEQUENCE: 10
acgctgactt tactgttcca aac 23

<210> SEQ ID NO 11
<211> LENGTH: 21
<212> TYPE: DNA
<213> ORGANISM: Artificial Sequence
<220> FEATURE:
<223> OTHER INFORMATION: synthetic sequence

<400> SEQUENCE: 11
aacatgattg ggatggaagt c 21

<210> SEQ ID NO 12
<211> LENGTH: 20
<212> TYPE: DNA
<213> ORGANISM: Artificial Sequence
<220> FEATURE:
<223> OTHER INFORMATION: synthetic sequence

<400> SEQUENCE: 12
gccgatgtgt gatgagatag 20

<210> SEQ ID NO 13
<211> LENGTH: 22
<212> TYPE: DNA
<213> ORGANISM: Artificial Sequence
<220> FEATURE:
<223> OTHER INFORMATION: synthetic sequence

<400> SEQUENCE: 13
aaacatgatt gggatggaag tc 22

<210> SEQ ID NO 14
<211> LENGTH: 22
<212> TYPE: DNA
<213> ORGANISM: Artificial Sequence
<220> FEATURE:
<223> OTHER INFORMATION: synthetic sequence

<400> SEQUENCE: 14
gccgatgtgt gatgagatag ag 22

<210> SEQ ID NO 15
<211> LENGTH: 22
<212> TYPE: DNA
<213> ORGANISM: Artificial Sequence
<220> FEATURE:
<223> OTHER INFORMATION: synthetic sequence

<400> SEQUENCE: 15

-continued gattgggatg gaagtccaat ac 22

<210> SEQ ID NO 16
<211> LENGTH: 25
<212> TYPE: DNA
<213> ORGANISM: Artificial Sequence
<220> FEATURE:
<223> OTHER INFORMATION: synthetic sequence

<400> SEQUENCE: 16
acacgctgac tttactgttc caaac 25

<210> SEQ ID NO 17
<211> LENGTH: 22
<212> TYPE: DNA
<213> ORGANISM: Artificial Sequence
<220> FEATURE:
<223> OTHER INFORMATION: synthetic sequence

<400> SEQUENCE: 17
atggctgccg atgtgtgatg ag 22

<210> SEQ ID NO 18
<211> LENGTH: 25
<212> TYPE: DNA
<213> ORGANISM: Artificial Sequence
<220> FEATURE:
<223> OTHER INFORMATION: synthetic sequence

<400> SEQUENCE: 18
gtgtctcaca ttttggtagc ttctc 25

<210> SEQ ID NO 19
<211> LENGTH: 22
<212> TYPE: DNA
<213> ORGANISM: Artificial Sequence
<220> FEATURE:
<223> OTHER INFORMATION: synthetic sequence

<400> SEQUENCE: 19
cttgggccac ccattgagta ac 22

<210> SEQ ID NO 20
<211> LENGTH: 21
<212> TYPE: DNA
<213> ORGANISM: Artificial Sequence
<220> FEATURE:
<223> OTHER INFORMATION: synthetic sequence

<400> SEQUENCE: 20
cgatgtgtga tgagatagag c 21

<210> SEQ ID NO 21
<211> LENGTH: 23
<212> TYPE: DNA
<213> ORGANISM: Artificial Sequence
<220> FEATURE:
<223> OTHER INFORMATION: synthetic sequence

<400> SEQUENCE: 21
tgattgggat ggaagtccaa tac 23

<210> SEQ ID NO 22
<211> LENGTH: 22
<212> TYPE: DNA
<213> ORGANISM: Artificial Sequence -continued
<220> FEATURE:
<223> OTHER INFORMATION: synthetic sequence

<400> SEQUENCE: 22
cgatgtgtga tgagatagag cg 22

<210> SEQ ID NO 23
<211> LENGTH: 25
<212> TYPE: DNA
<213> ORGANISM: Artificial Sequence
<220> FEATURE:
<223> OTHER INFORMATION: synthetic sequence

<400> SEQUENCE: 23
catgattggg atggaagtcc aatac 25

<210> SEQ ID NO 24
<211> LENGTH: 24
<212> TYPE: DNA
<213> ORGANISM: Artificial Sequence
<220> FEATURE:
<223> OTHER INFORMATION: synthetic sequence

<400> SEQUENCE: 24
ccaagtgtct cacattttgg tagc 24

<210> SEQ ID NO 25
<211> LENGTH: 20
<212> TYPE: DNA
<213> ORGANISM: Artificial Sequence
<220> FEATURE:
<223> OTHER INFORMATION: synthetic sequence

<400> SEQUENCE: 25
tgggccaccc attgagtaac 20

<210> SEQ ID NO 26
<211> LENGTH: 18
<212> TYPE: DNA
<213> ORGANISM: Artificial Sequence
<220> FEATURE:
<223> OTHER INFORMATION: synthetic sequence

<400> SEQUENCE: 26
aggtagtggt attaacgg 18

<210> SEQ ID NO 27
<211> LENGTH: 20
<212> TYPE: DNA
<213> ORGANISM: Artificial Sequence
<220> FEATURE:
<223> OTHER INFORMATION: synthetic sequence

<400> SEQUENCE: 27
agatacttca agctctattc 20

<210> SEQ ID NO 28
<211> LENGTH: 20
<212> TYPE: DNA
<213> ORGANISM: Artificial Sequence
<220> FEATURE:
<223> OTHER INFORMATION: synthetic sequence

<400> SEQUENCE: 28
tcataagata cttcaagctc 20

-continued

<210> SEQ ID NO 29
<211> LENGTH: 19
<212> TYPE: DNA
<213> ORGANISM: Artificial Sequence
<220> FEATURE:
<223> OTHER INFORMATION: synthetic sequence

<400> SEQUENCE: 29
cttctctacc tggagtatc 19

<210> SEQ ID NO 30
<211> LENGTH: 21
<212> TYPE: DNA
<213> ORGANISM: Artificial Sequence
<220> FEATURE:
<223> OTHER INFORMATION: synthetic sequence

<400> SEQUENCE: 30
gcttatagag tagcttaaac c 21

<210> SEQ ID NO 31
<211> LENGTH: 18
<212> TYPE: DNA
<213> ORGANISM: Artificial Sequence
<220> FEATURE:
<223> OTHER INFORMATION: synthetic sequence

<400> SEQUENCE: 31
caggtagtgg tattaacg 18

<210> SEQ ID NO 32
<211> LENGTH: 19
<212> TYPE: DNA
<213> ORGANISM: Artificial Sequence
<220> FEATURE:
<223> OTHER INFORMATION: synthetic sequence

<400> SEQUENCE: 32
cataagatac ttcaagctc 19

<210> SEQ ID NO 33
<211> LENGTH: 19
<212> TYPE: DNA
<213> ORGANISM: Artificial Sequence
<220> FEATURE:
<223> OTHER INFORMATION: synthetic sequence

<400> SEQUENCE: 33
gatacttcaa gctctattc 19

<210> SEQ ID NO 34
<211> LENGTH: 20
<212> TYPE: DNA
<213> ORGANISM: Artificial Sequence
<220> FEATURE:
<223> OTHER INFORMATION: synthetic sequence

<400> SEQUENCE: 34
gcttatagag tagcttaaac 20

<210> SEQ ID NO 35
<211> LENGTH: 20
<212> TYPE: DNA
<213> ORGANISM: Artificial Sequence
<220> FEATURE:
<223> OTHER INFORMATION: synthetic sequence -continued

<400> SEQUENCE: 35
ctacctggag tatcattttc 20

<210> SEQ ID NO 36
<211> LENGTH: 21
<212> TYPE: DNA
<213> ORGANISM: Artificial Sequence
<220> FEATURE:
<223> OTHER INFORMATION: synthetic sequence

<400> SEQUENCE: 36
ggcttataga gtagcttaaa c 21

<210> SEQ ID NO 37
<211> LENGTH: 18
<212> TYPE: DNA
<213> ORGANISM: Artificial Sequence
<220> FEATURE:
<223> OTHER INFORMATION: synthetic sequence

<400> SEQUENCE: 37
aatatcttct ctacctgg 18

<210> SEQ ID NO 38
<211> LENGTH: 18
<212> TYPE: DNA
<213> ORGANISM: Artificial Sequence
<220> FEATURE:
<223> OTHER INFORMATION: synthetic sequence

<400> SEQUENCE: 38
agttttcata acaagtgc 18

<210> SEQ ID NO 39
<211> LENGTH: 25
<212> TYPE: DNA
<213> ORGANISM: Artificial Sequence
<220> FEATURE:
<223> OTHER INFORMATION: synthetic sequence

<400> SEQUENCE: 39
cttctctacc tggagtatca ttttc 25

<210> SEQ ID NO 40
<211> LENGTH: 26
<212> TYPE: DNA
<213> ORGANISM: Artificial Sequence
<220> FEATURE:
<223> OTHER INFORMATION: synthetic sequence

<400> SEQUENCE: 40
gagtagctta aacctaactt tccttg 26

<210> SEQ ID NO 41
<211> LENGTH: 22
<212> TYPE: DNA
<213> ORGANISM: Artificial Sequence
<220> FEATURE:
<223> OTHER INFORMATION: synthetic sequence

<400> SEQUENCE: 41
gagtagctta aacctaactt tc 22

<210> SEQ ID NO 42

-continued

<211> LENGTH: 18
<212> TYPE: DNA
<213> ORGANISM: Artificial Sequence
<220> FEATURE:
<223> OTHER INFORMATION: synthetic sequence

<400> SEQUENCE: 42
tcataagata cttcaagc 18

<210> SEQ ID NO 43
<211> LENGTH: 22
<212> TYPE: DNA
<213> ORGANISM: Artificial Sequence
<220> FEATURE:
<223> OTHER INFORMATION: synthetic sequence

<400> SEQUENCE: 43
ctctacctgg agtatcattt tc 22

<210> SEQ ID NO 44
<211> LENGTH: 18
<212> TYPE: DNA
<213> ORGANISM: Artificial Sequence
<220> FEATURE:
<223> OTHER INFORMATION: synthetic sequence

<400> SEQUENCE: 44
acctggagta tcattttc 18

<210> SEQ ID NO 45
<211> LENGTH: 18
<212> TYPE: DNA
<213> ORGANISM: Artificial Sequence
<220> FEATURE:
<223> OTHER INFORMATION: synthetic sequence

<400> SEQUENCE: 45
tctgggctta tagagtag 18

<210> SEQ ID NO 46
<211> LENGTH: 18
<212> TYPE: DNA
<213> ORGANISM: Artificial Sequence
<220> FEATURE:
<223> OTHER INFORMATION: synthetic sequence

<400> SEQUENCE: 46
ctgggcttat agagtagc 18

<210> SEQ ID NO 47
<211> LENGTH: 1607
<212> TYPE: DNA
<213> ORGANISM: JAKE strain, Ehrlichia canis p30

<400> SEQUENCE: 47
attttattta ttaccaatct tatataatat attaaatttc tcttacaaaa atctctaatg 60
ttttatacct aatatatata ttctggcttg tatctacttt gcacttccac tattgttaat 120
ttattttcac tattttaggt gtaatatgaa ttgcaaaaaa attcttataa caactgcatt 180
aatatcatta atgtactcta ttccaagcat atctttttct gatactatac aagatggtaa 240
catgggtggt aacttctata ttagtggaaa gtatgtacca agtgtctcac attttggtag 300
cttctcagct aaagaagaaa gcaaatcaac tgttggagtt tttggattaa aacatgattg 360
ggatggaagt ccaatactta agaataaaca cgctgacttt actgttccaa actattcgtt 420

-continued

```
cagatacgag aacaatccat ttctagggtt tgcaggagct atcggttact caatgggtgg    480
cccaagaata gaattcgaaa tatcttatga agcattcgac gtaaaaagtc ctaatatcaa    540
ttatcaaaat gacgcgcaca ggtactgcgc tctatctcat cacacatcgg cagccatgga    600
agctgataaa tttgtcttct taaaaaacga agggttaatt gacatatcac ttgcaataaa    660
tgcatgttat gatataataa atgacaaagt acctgtttct ccttatatat gcgcaggtat    720
tggtactgat ttgatttcta tgtttgaagc tacaagtcct aaaatttcct accaaggaaa    780
actgggcatt agttactcta ttaatccgga aacctctgtt ttcatcggtg ggcatttcca    840
caggatcata ggtaatgagt ttagagatat tcctgcaata gtacctagta actcaactac    900
aataagtgga ccacaatttg caacagtaac actaaatgtg tgtcactttg gtttagaact    960
tggaggaaga tttaacttct aattttattg ttgccacata ttaaaaatga tctaaacttg   1020
tttttawtat tgctacatac aaaaaaagaa aaatagtggc aaaagaatgt agcaataaga   1080
ggggggggg ggaccaaatt tatcttctat gcttcccaag ttttttcycg ctatttatga    1140
cttaaacaac agaaggtaat atcctcacgg aaaacttatc ttcaaatatt ttatttatta   1200
ccaatcttat ataatatatt aaatttctct tacaaaaatc actagtattt tataccaaaa   1260
tatatattct gacttgcttt tcttctgcac ttctactatt tttaatttat ttgtcactat   1320
taggttataa taawatgaat tgcmaaagat ttttcatagc aagtgcattg atatcactaa   1380
tgtctttctt acctagcgta tctttttctg aatcaataca tgaagataat ataaatggta   1440
acttttacat tagtgcaaag tatatgccaa gtgcctcaca ctttggcgta ttttcagtta   1500
aagaagagaa aaacacaaca actggagttt tcggattaaa acaagattgg gacggagcaa   1560
cactaaagga tgcaagcwgc agccacacaw tagacccaag tacaatg                 1607
```

<210> SEQ ID NO 48
<211> LENGTH: 849
<212> TYPE: DNA
<213> ORGANISM: ORF sequence, Ehrlichia chaffeensis p28

<400> SEQUENCE: 48

```
atgaattaca aaaaagtttt cataacaagt gcattgatat caytaatatc ttctctacct     60
ggagtatcat tttcygaccc arcaggtagt ggtattaacg gyaatttcta yatcagtgga    120
aaatayatgc caagygcttc gcattttggr gtrttytctg ctaaggaaga aagaartaca    180
acagytggag trtttggayt gaagcaarat tgggayggma gygcaatayc ymacwcyhmy    240
mswrahrmtv yattyactgt ytcaaaytay tcrtttaaat atgaaaayaa yccrtttyta    300
ggwtttgcag gagctattgg ytactcaatg gatggyccaa gaatagagct tgaagtatct    360
tatgaracat tygatgtwaa aaatcaaggt aacarytaya agaaygaagc dcatagrtay    420
tgtgctytat cycrtmasrs ywcarbarca rrcatgwska gtgcarrtra tamwtttgty    480
tttctaaaaa atgaaggryt acttgacrta tcrttyatgc tgaacgcatg ctatgaygta    540
rtargygaag gmataccttt ttctccttay atatgygyag gtatyggkac tgatttagta    600
tccatgtttg aagytacaaa ycctaaaatt tcttaccaag gaaagttagg tttaagctac    660
tctataagcc cagaarcttc tgtstttrty ggyggrcayt tycataaggt ratrggraac    720
gaattyagag atattcctrc trtaatacct avtggatcaa swcttgcagg aamaggraay    780
yaccctgcaa tagtaayact rgaygtatgc cactttggwa tagarcttgg aggaagrttt    840
gctttctaa                                                            849
```

-continued

```
<210> SEQ ID NO 49
<211> LENGTH: 22
<212> TYPE: DNA
<213> ORGANISM: Artificial Sequence
<220> FEATURE:
<223> OTHER INFORMATION: synthetic sequence

<400> SEQUENCE: 49

ggcttataga gtagcttaaa cc                                   22


<210> SEQ ID NO 50
<211> LENGTH: 24
<212> TYPE: DNA
<213> ORGANISM: Artificial Sequence
<220> FEATURE:
<223> OTHER INFORMATION: synthetic sequence

<400> SEQUENCE: 50

ttctctacct ggagtatcat tttc                                 24


<210> SEQ ID NO 51
<211> LENGTH: 26
<212> TYPE: DNA
<213> ORGANISM: Artificial Sequence
<220> FEATURE:
<223> OTHER INFORMATION: synthetic sequence

<400> SEQUENCE: 51

ggcttataga gtagcttaaa cctaac                               26
```